US008146331B2

(12) United States Patent  (10) Patent No.: US 8,146,331 B2
Soloman  (45) Date of Patent: Apr. 3, 2012

(54) AUTOMATED PACKAGING, INSPECTION, VERIFICATION, AND COUNTING APPARATUS

(75) Inventor: Sabrie Soloman, Saddle River, NJ (US)

(73) Assignee: Sabrie Soloman, Saddle River, NJ (US)

( * ) Notice: Subject to any disclaimer, the term of this patent is extended or adjusted under 35 U.S.C. 154(b) by 42 days.

(21) Appl. No.: 12/354,561

(22) Filed: Jan. 15, 2009

(65) Prior Publication Data

US 2010/0175352 A1 Jul. 15, 2010

(51) Int. Cl.
B65B 1/04 (2006.01)
B65B 57/18 (2006.01)

(52) U.S. Cl. .......... 53/493; 53/151; 53/244; 53/250

(58) Field of Classification Search ............ 53/151–154, 53/244, 248–250, 473, 493–495, 498, 500, 53/900; 221/131, 160, 167, 168, 266, 278
See application file for complete search history.

(56) References Cited

U.S. PATENT DOCUMENTS

| | | | | |
|---|---|---|---|---|
| 3,354,607 A | * | 11/1967 | Lakso | 53/167 |
| 3,417,542 A | * | 12/1968 | Merrill et al. | 53/167 |
| 4,018,358 A | * | 4/1977 | Johnson et al. | 221/7 |
| 4,094,439 A | * | 6/1978 | List | 221/9 |
| 4,353,456 A | * | 10/1982 | Yamamoto | 198/397.04 |
| 4,674,259 A | * | 6/1987 | Hills | 53/202 |
| 5,489,980 A | * | 2/1996 | Anthony | 356/308 |
| 5,806,686 A | * | 9/1998 | Ecker | 209/615 |
| 5,884,806 A | * | 3/1999 | Boyer et al. | 221/75 |
| 5,996,768 A | * | 12/1999 | Boyce et al. | 198/397.01 |
| 6,185,901 B1 | * | 2/2001 | Aylward | 53/250 |
| 6,363,687 B1 | * | 4/2002 | Luciano et al. | 53/55 |
| 6,522,945 B2 | * | 2/2003 | Sleep et al. | 700/225 |
| 6,574,580 B2 | * | 6/2003 | Hamilton | 702/128 |
| 6,681,550 B1 | * | 1/2004 | Aylward | 53/473 |
| 6,738,723 B2 | * | 5/2004 | Hamilton | 702/128 |
| 6,799,413 B2 | * | 10/2004 | Aylward | 53/473 |
| 7,139,639 B2 | * | 11/2006 | Broussard et al. | 700/225 |
| 7,255,247 B2 | * | 8/2007 | Aylward | 221/168 |
| 7,765,776 B1 | * | 8/2010 | Leu et al. | 53/467 |
| 2002/0104741 A1 | * | 8/2002 | Buckley et al. | 198/803.14 |
| 2002/0113076 A1 | * | 8/2002 | Collins et al. | 221/76 |
| 2004/0011806 A1 | * | 1/2004 | Luciano et al. | 221/266 |
| 2005/0288906 A1 | * | 12/2005 | Drennen et al. | 702/189 |
| 2006/0025884 A1 | * | 2/2006 | Henkel | 700/216 |
| 2006/0088196 A1 | * | 4/2006 | Popovich et al. | 382/128 |
| 2006/0180234 A1 | * | 8/2006 | Aylward | 141/71 |
| 2008/0061074 A1 | * | 3/2008 | Remis et al. | 221/69 |
| 2010/0115892 A1 | * | 5/2010 | Aylward et al. | 53/473 |
| 2010/0139222 A1 | * | 6/2010 | Federle et al. | 53/474 |

* cited by examiner

Primary Examiner — Hemant M Desai
(74) Attorney, Agent, or Firm — Accupatents

(57) ABSTRACT

The present invention is an automated packaging apparatus utilizing a rotating assembly of elongated slats containing cavities to receive discrete pharmaceutical, vitamin, or food products. Quantities of discrete products such as tablets, capsules, or gels are deposited into the hopper of the apparatus. The apparatus then dispenses the discrete products into containers moving on a conveyor system such that each container receives a predetermined quality and quantity of pharmaceutical, vitamin, or food products. While operating at high speed, the apparatus inspects, counts, identifies and analyzes each product deposited into the containers and maintains electronic records describing the status of each product. In the event any errors occur the apparatus produces various alerts to inform the operator. The presence of foreign products or objects may cause the apparatus to instantly stop the entire system including peripheral equipment. A series of Good Manufacturing Practice protocols can then be enforced as per FDA requirements.

20 Claims, 30 Drawing Sheets

10

A Perspective View of Automated Packaging, Counting, Verification, and Inspection Apparatus

160

Close up Perspective View of the Invention, Illustrating the Rake Assembly and its Relative Location in the Present Invention

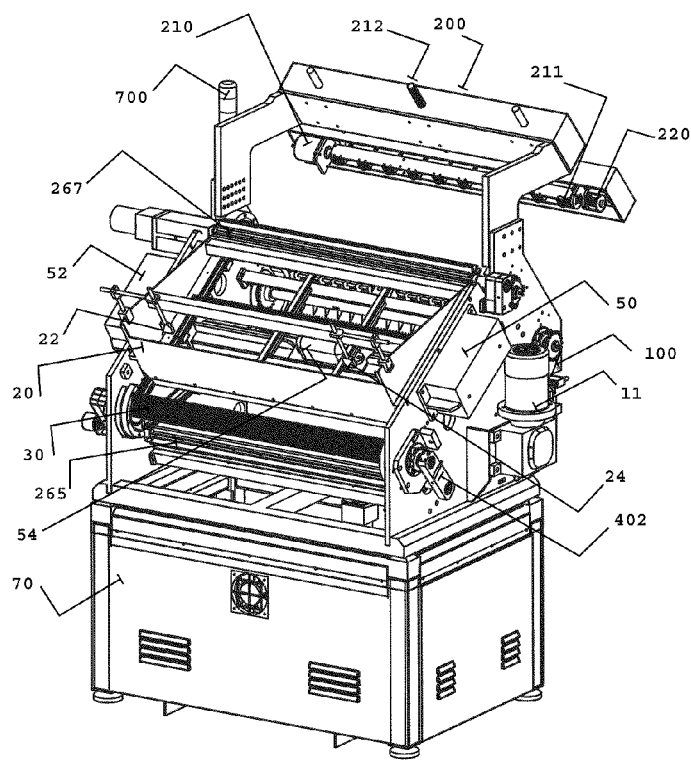
Figure 1, A Perspective View of Automated Packaging, Counting, Verification, and Inspection Apparatus

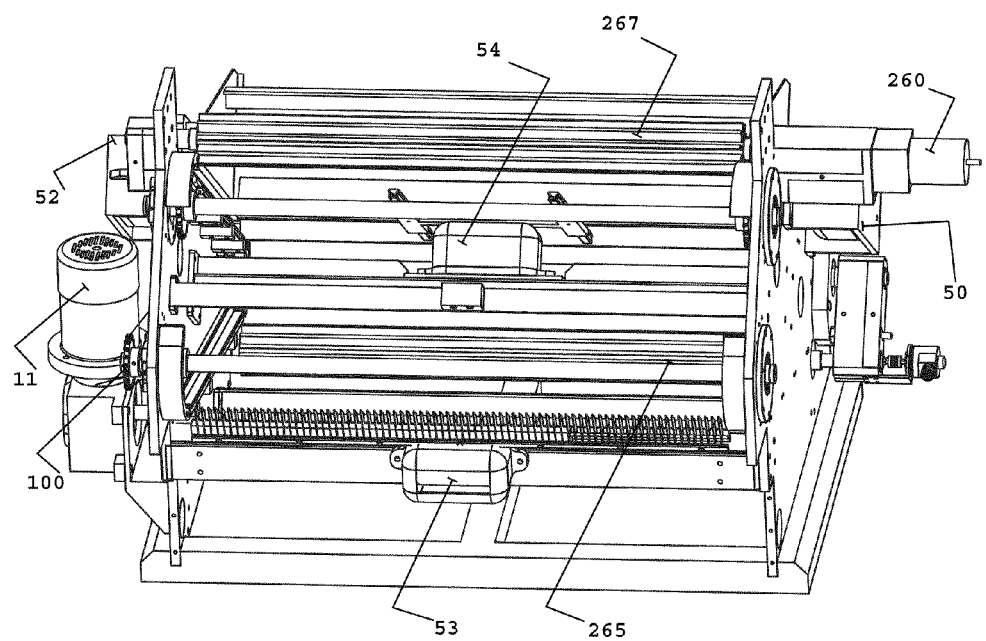
Figure 1.1, A Perspective View of the Upper Part of the Apparatus Illustrating its Vibrating Motors, and its Upper and Lower Brush Mechanisms

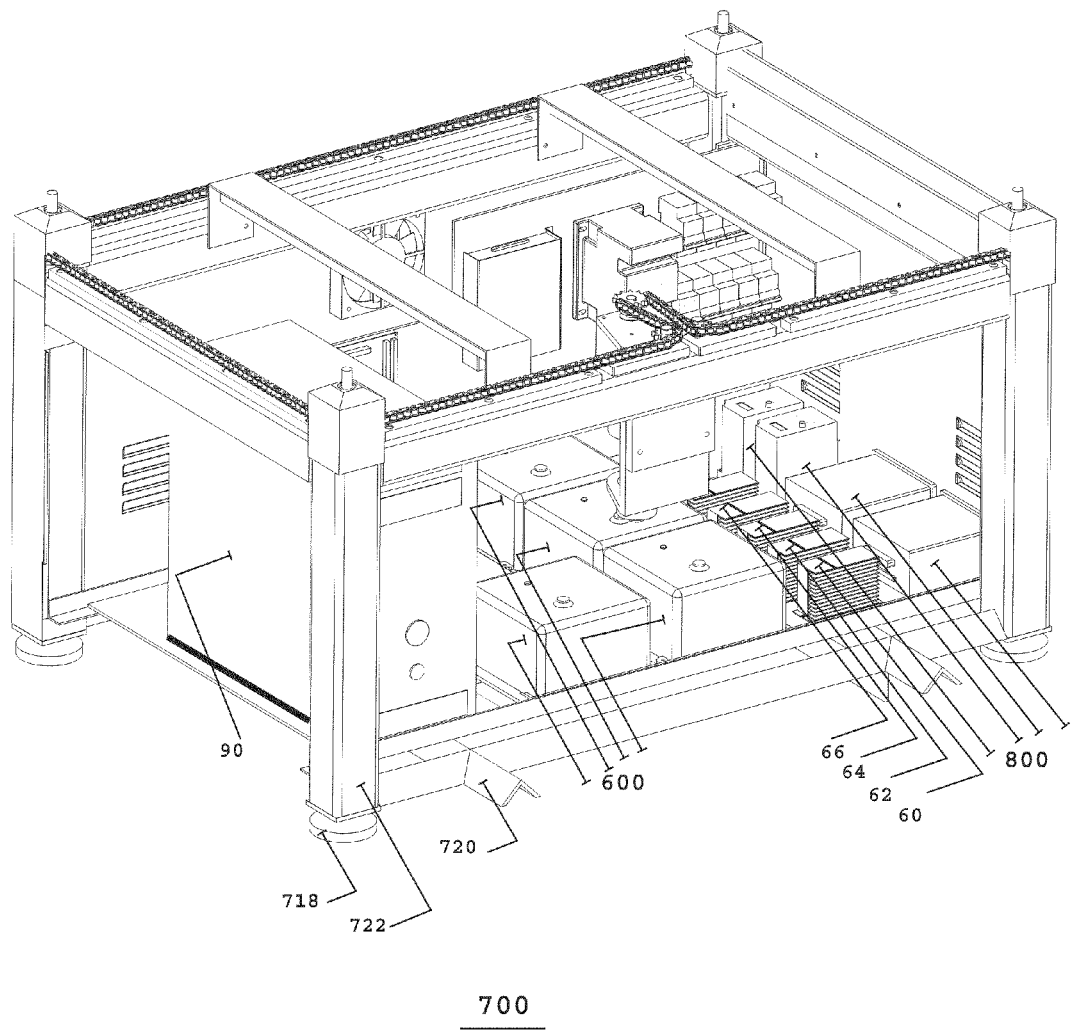
Figure 1.2, A Perspective View of the Lower Part of the Apparatus Representing its Base Structure, PLC Control, Workstation PC Control, and its Apparatus Lift Mechanisms

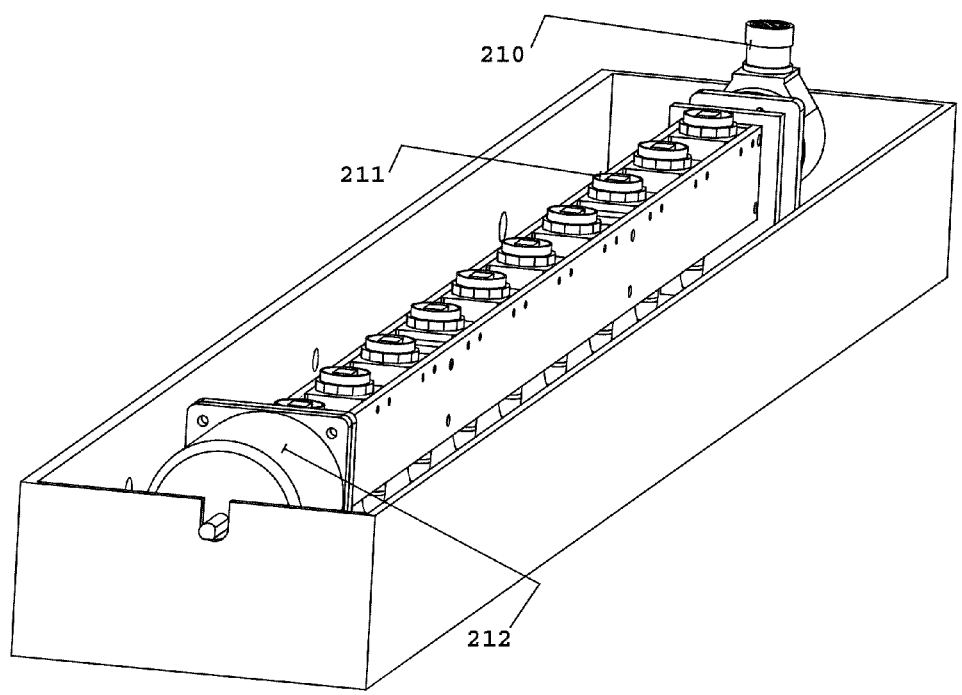
Figure 1.3, A Perspective View of the Apparatus Illustrating its Automatic Vision Inspection System

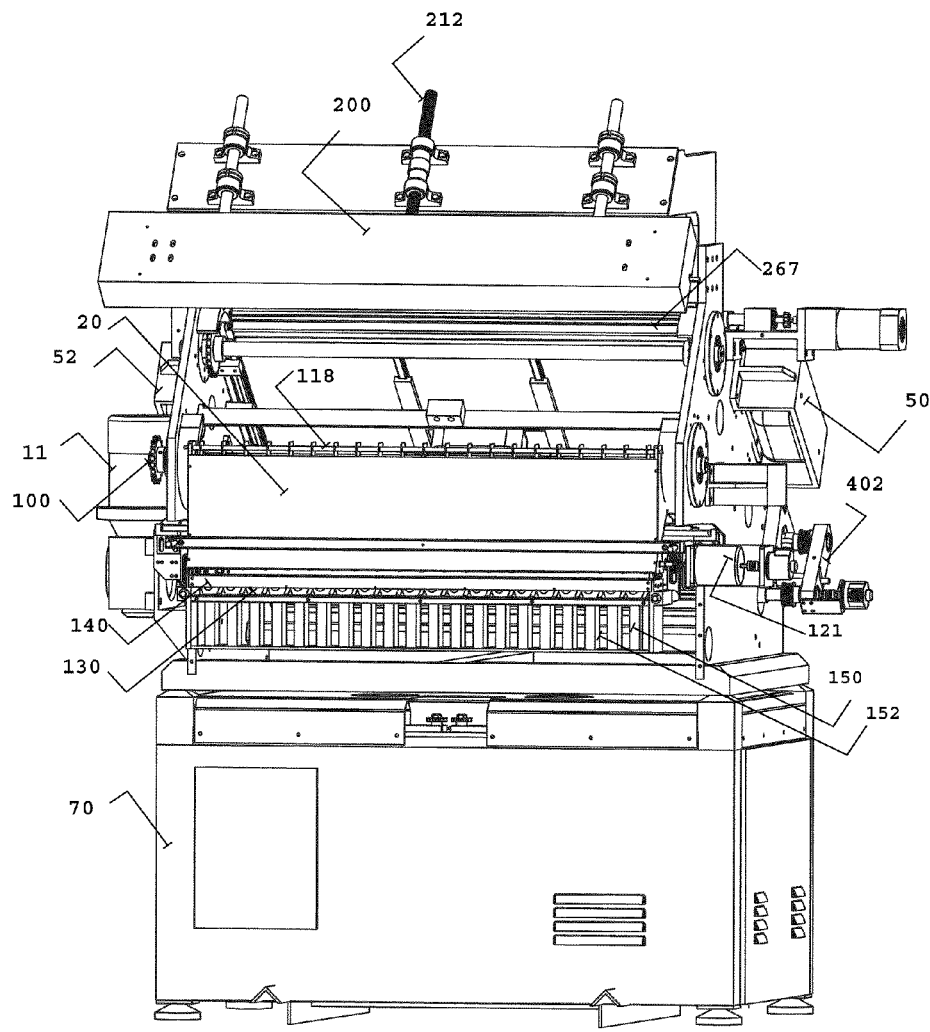
Figure 2, A Perspective Front View of the Automated Packaging Apparatus of the Present Invention

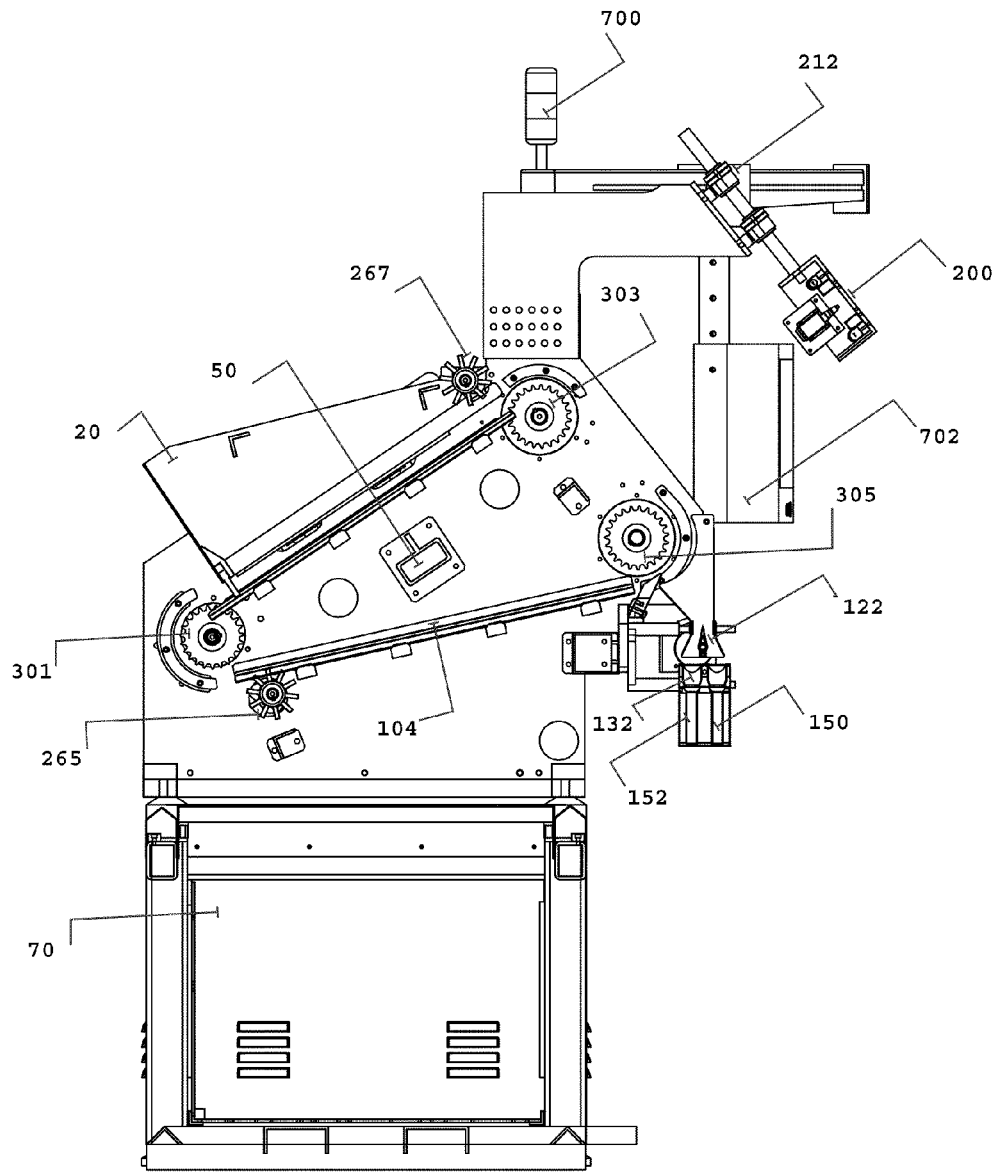
Figure 3, Left Side of Invention Illustrating the Drive and the Inspection Mechanisms of the Present Invention

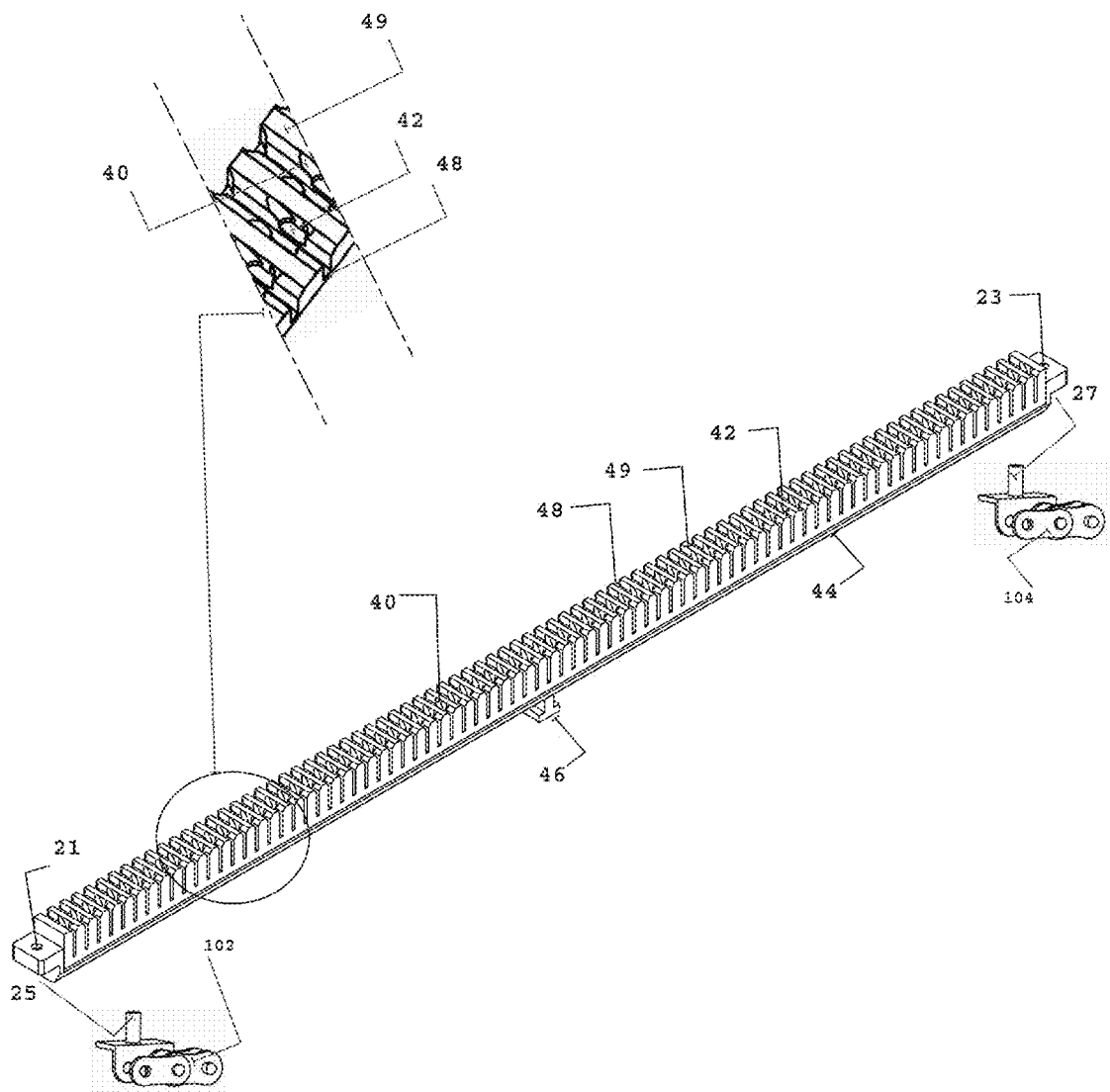
Figure 4, Perspective Views Illustrating a Slat with Cavities, and its Corresponding Engaging Pins of the Present Invention

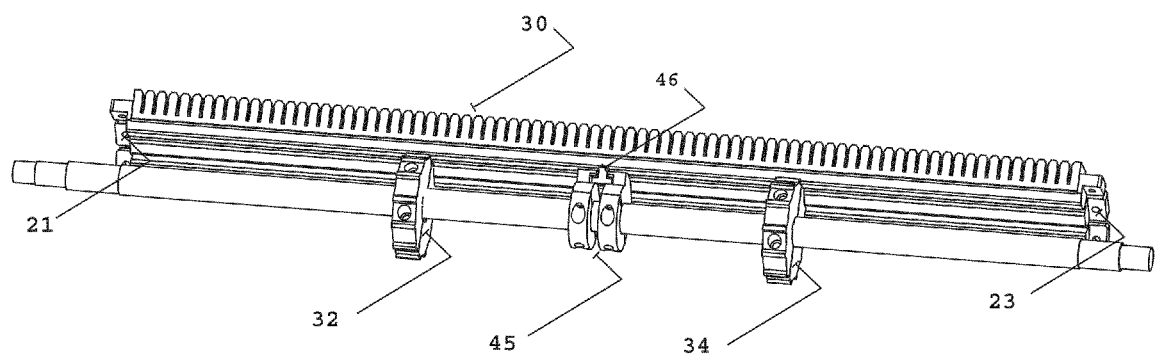
Figure 4.1, A Perspective View Illustrating the Synchronized
Motion of Slat Prior to Dispensing Products of
the Present Invention

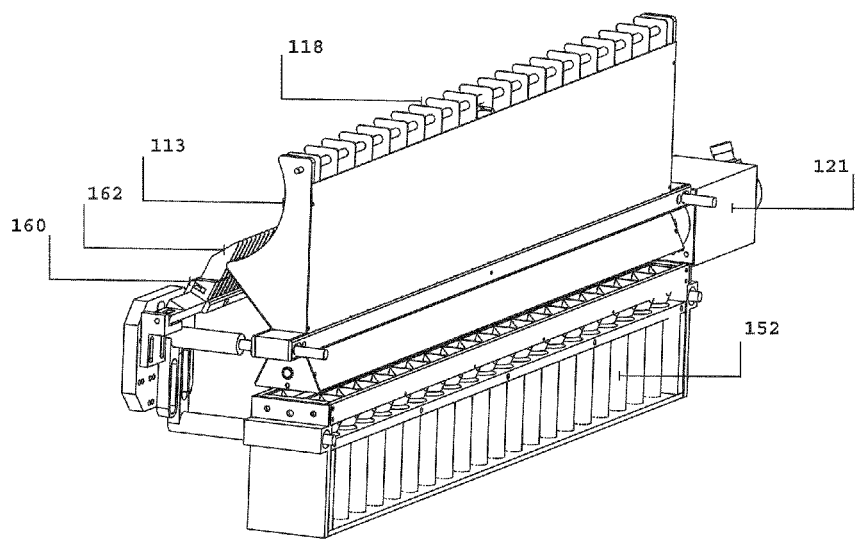
Figure 5, Close up Perspective View of the Invention, Illustrating the Rake Assembly and its Relative Location in the Present Invention

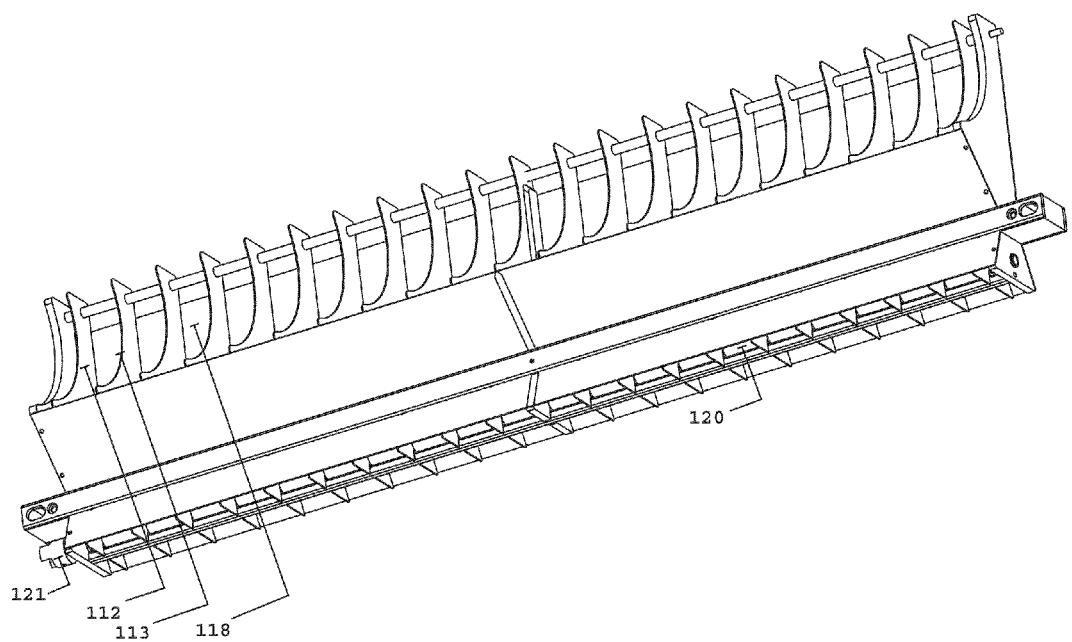
Figure 6, A Close up Perspective View, Illustrating the Divider Assembly of the Present Invention

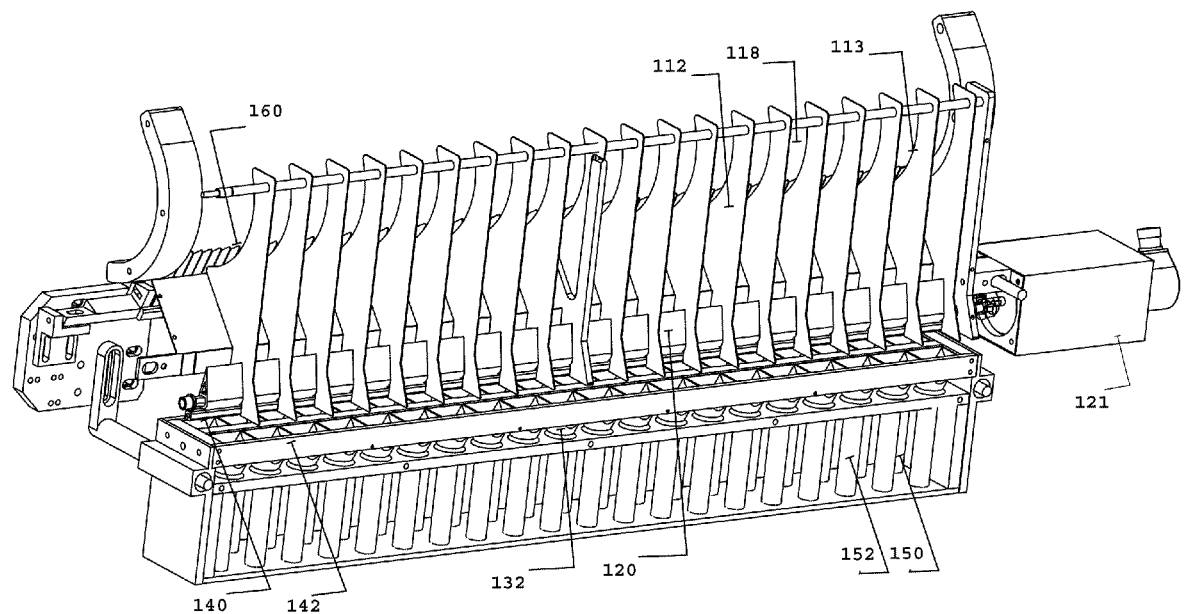
Figure 6.1, A Close up Perspective View of the Invention, Illustrating the Divider Assembly Configured with the Diverter Assembly of the Present Invention

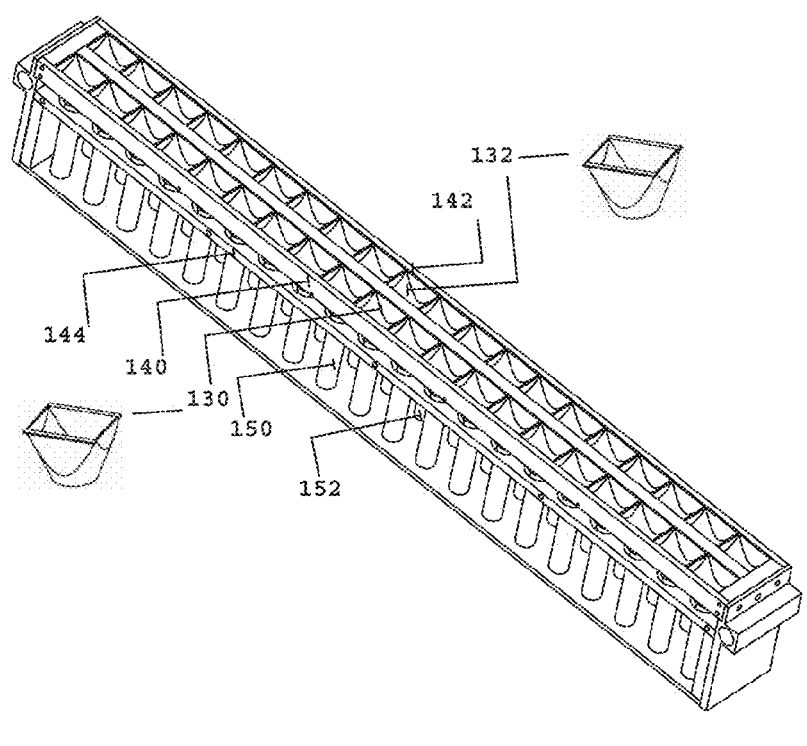
Figure 7, A Close up Perspective View of the Invention, Illustrating the Dispenser Assembly

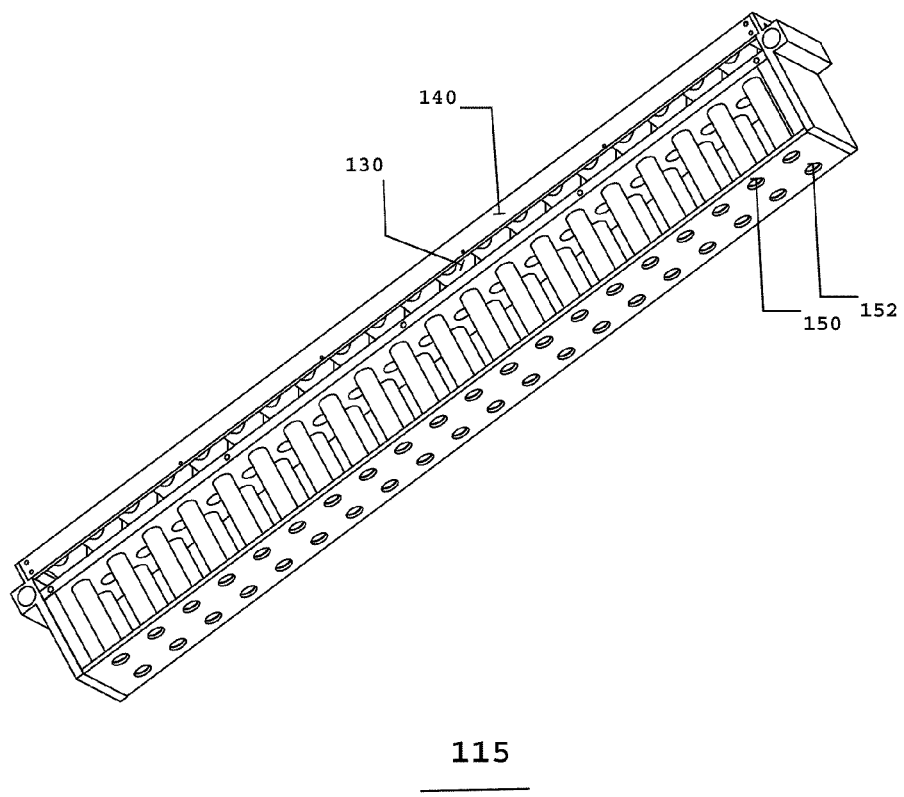
Figure 7.1, A Close up View of the Invention, Illustrating the Location of Products Exiting the Dispenser Assembly

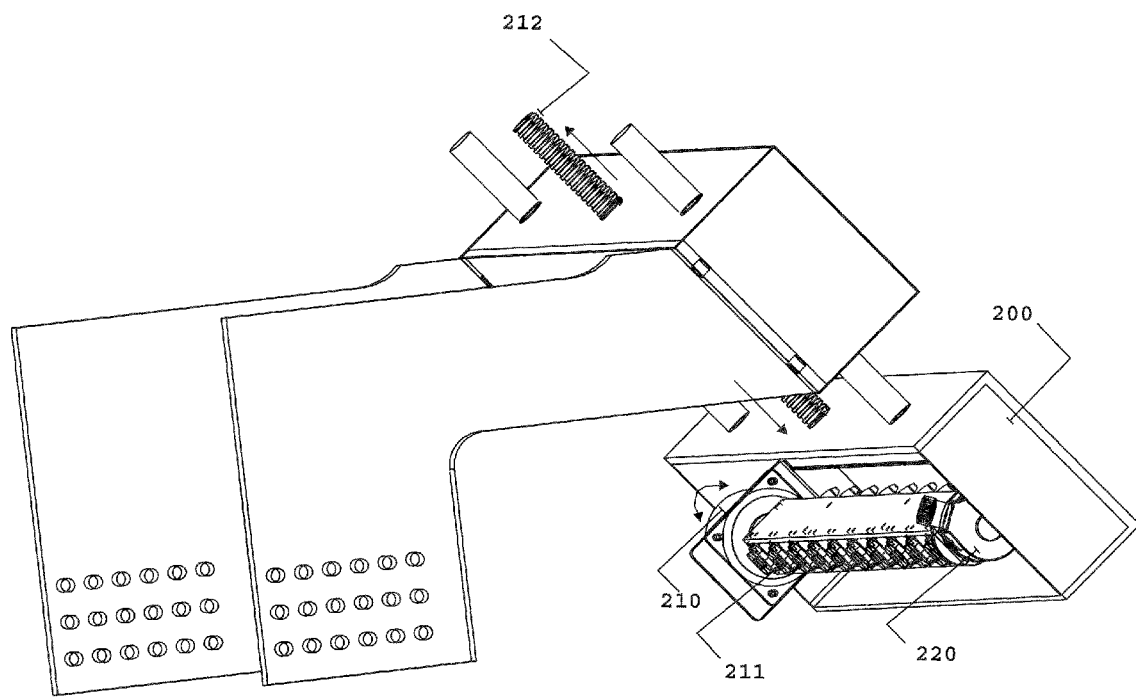
Figure 8, A Perspective View Illustrating the Vision Inspection System of the Present Invention

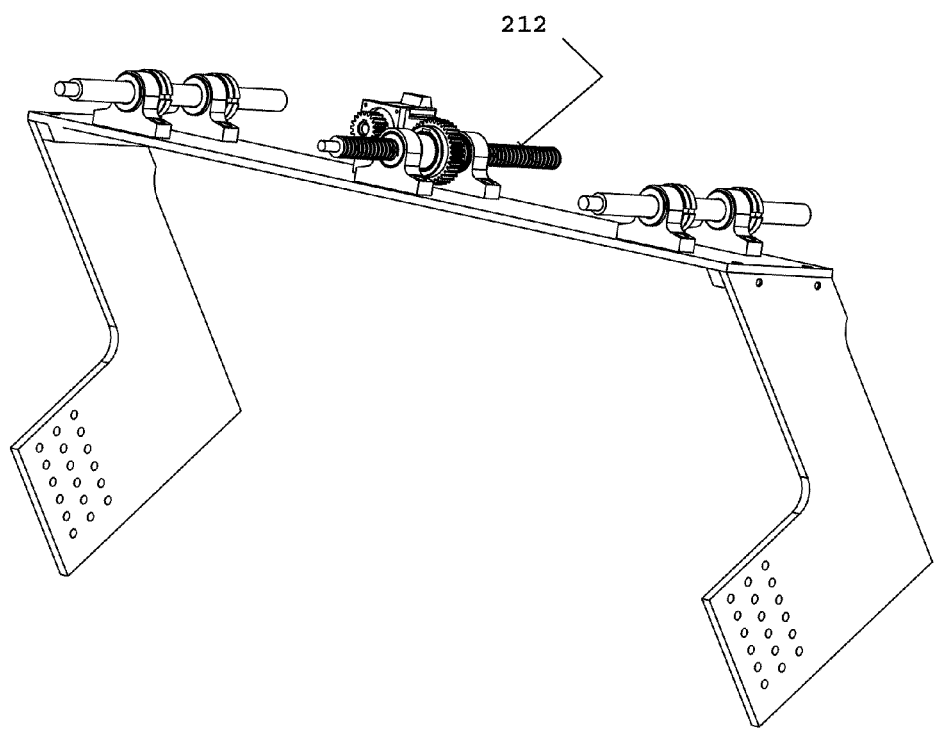
212
Figure 8.1, A Perspective View Illustrating the Linear Drive Mechanism of the Vision Inspection System of the Present Invention

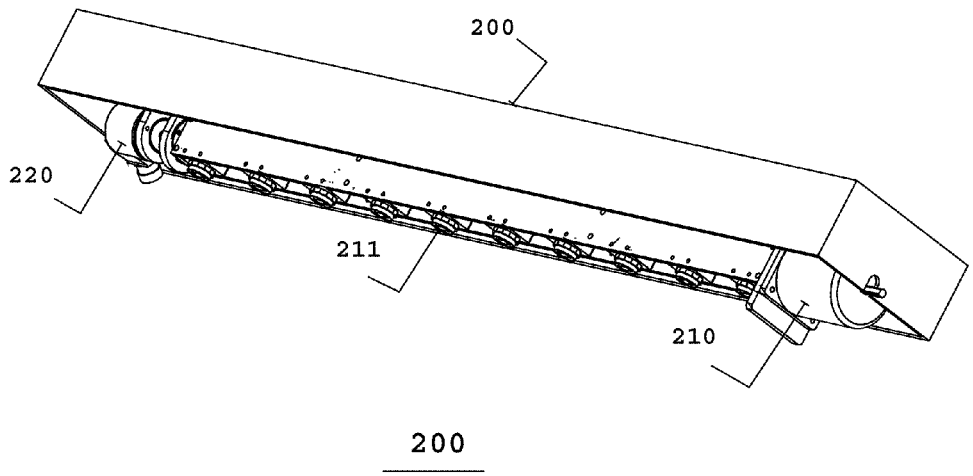
Figure 8.2, A Perspective View Illustrating the Rotational Drive Mechanism of the Vision Inspection System of the Present Invention

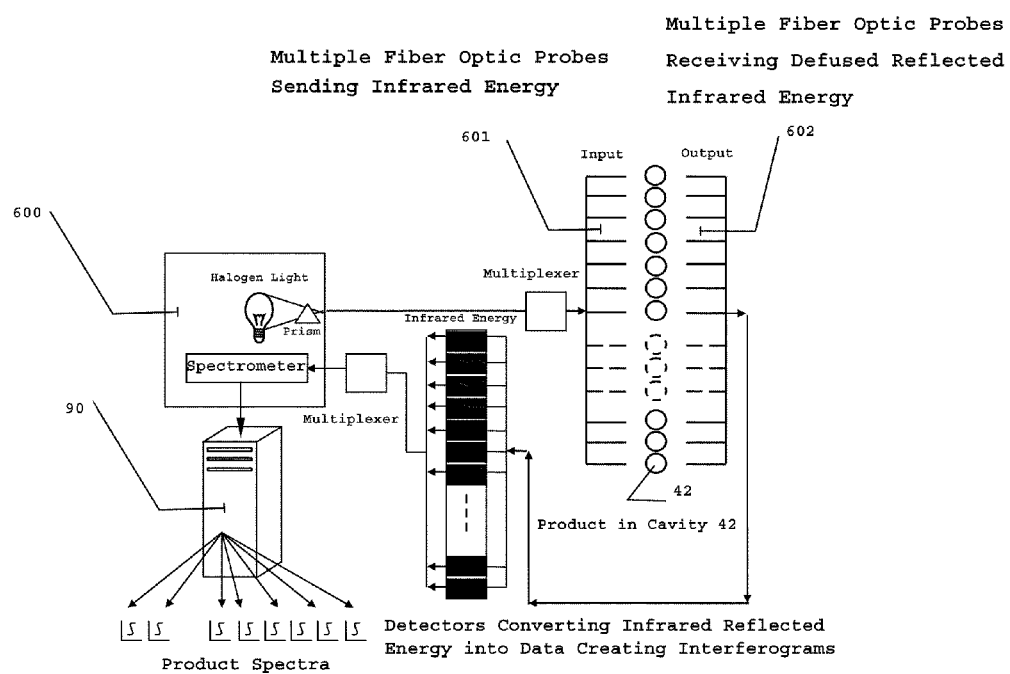
Figure 9, A close up Schematic Diagram of the Invention, Illustrating The Spectroscopy System of the Present Invention

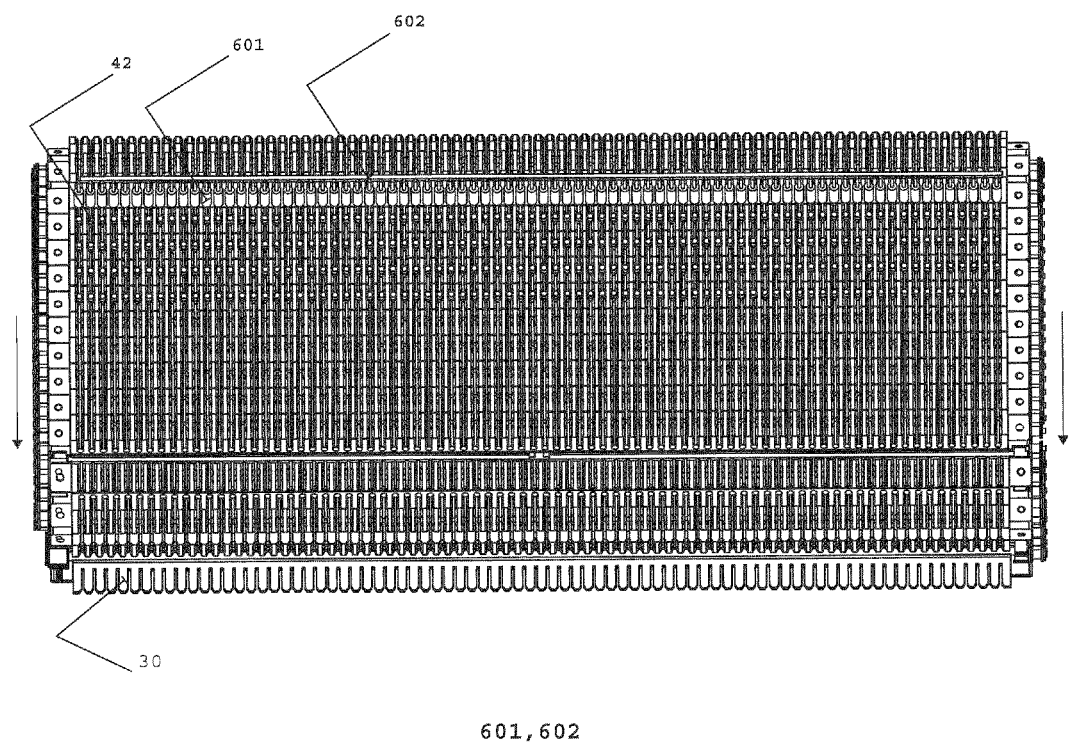
601,602
Figure 9.1, A Perspective View of the Invention, Illustrating the Spectroscopy Probes to Convey and Receive Infrared Energies in the Present Invention

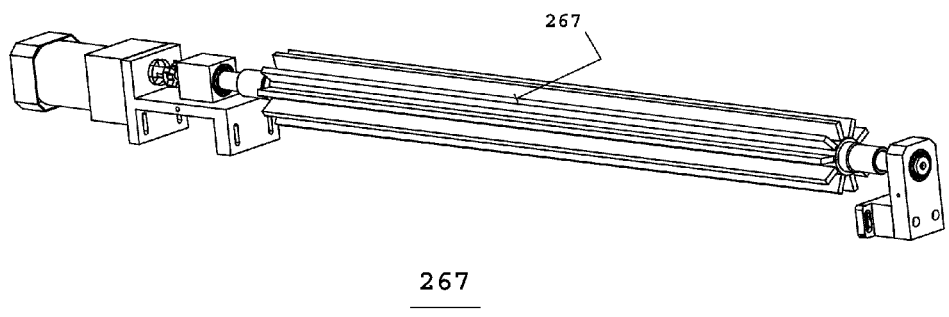
267
Figure 10.1, A Perspective View of the Present Invention, Illustrating the Upper Brush Assembly

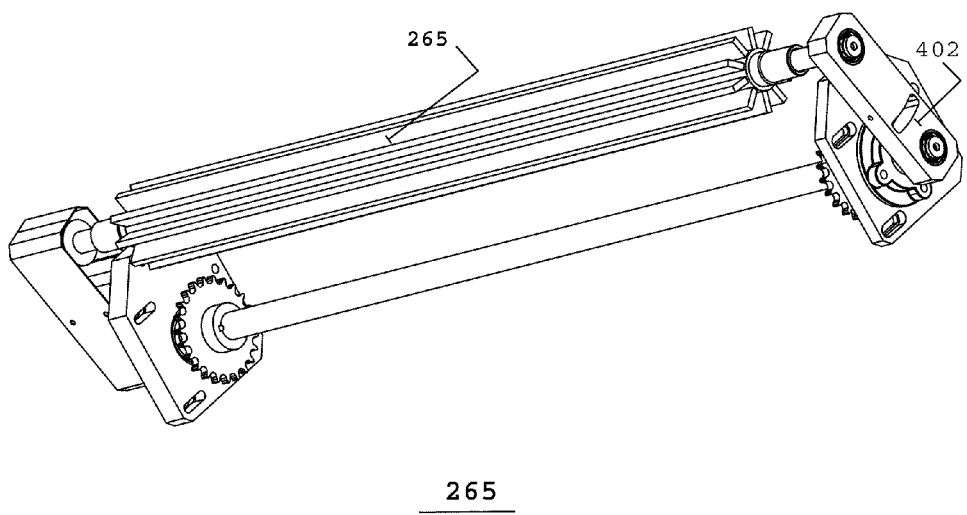
Figure 10.2, A Close up Perspective View of the Present Invention Illustrating the Lower Brush Assembly

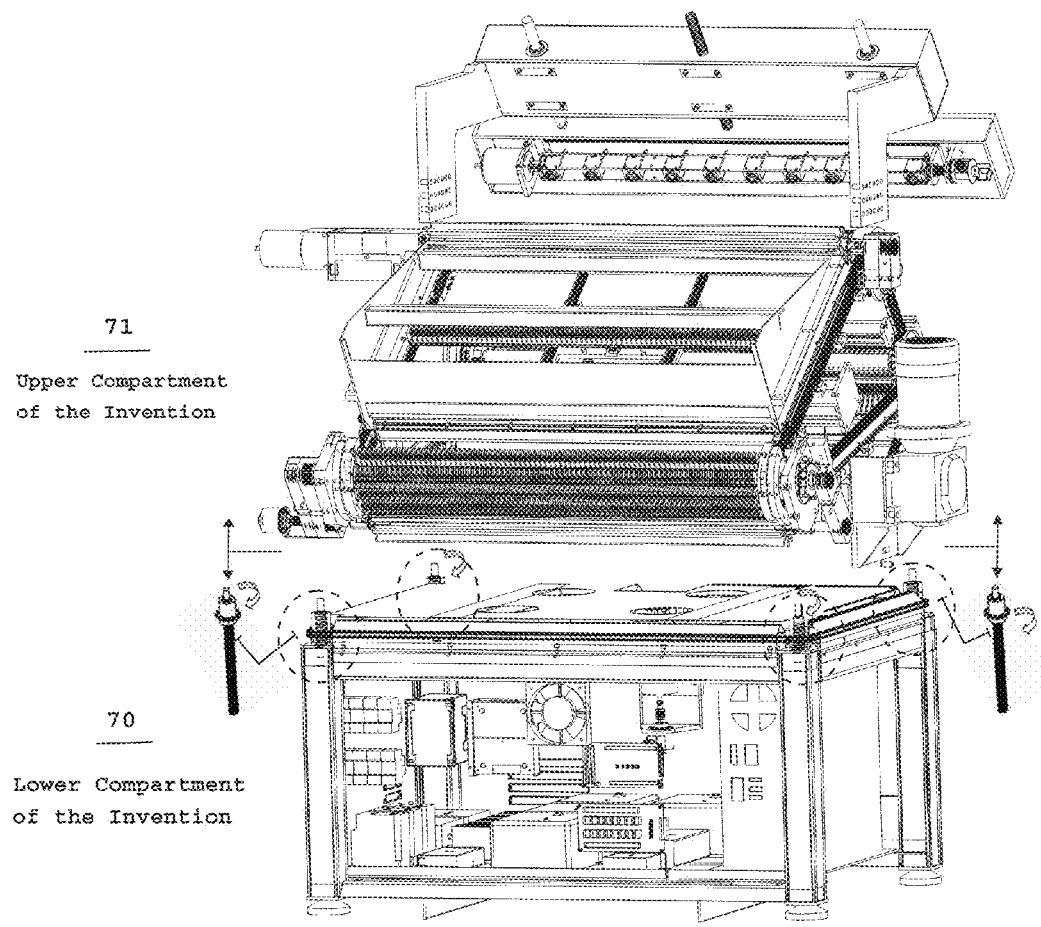
Figure 11, Perspective Views of the Upper and Lower Compartments of the Present Invention

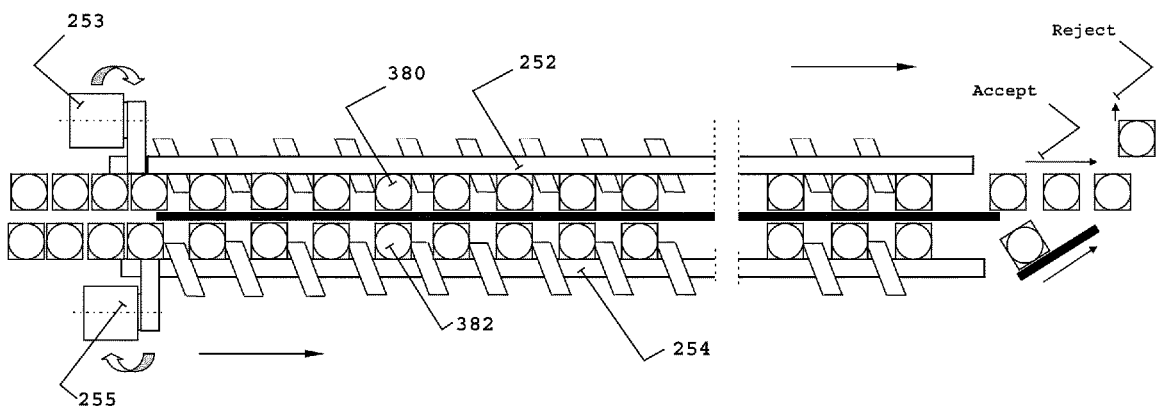
Figure 11.1, A Schematic Illustration of the Timing Screw Mechanism of the Present Invention

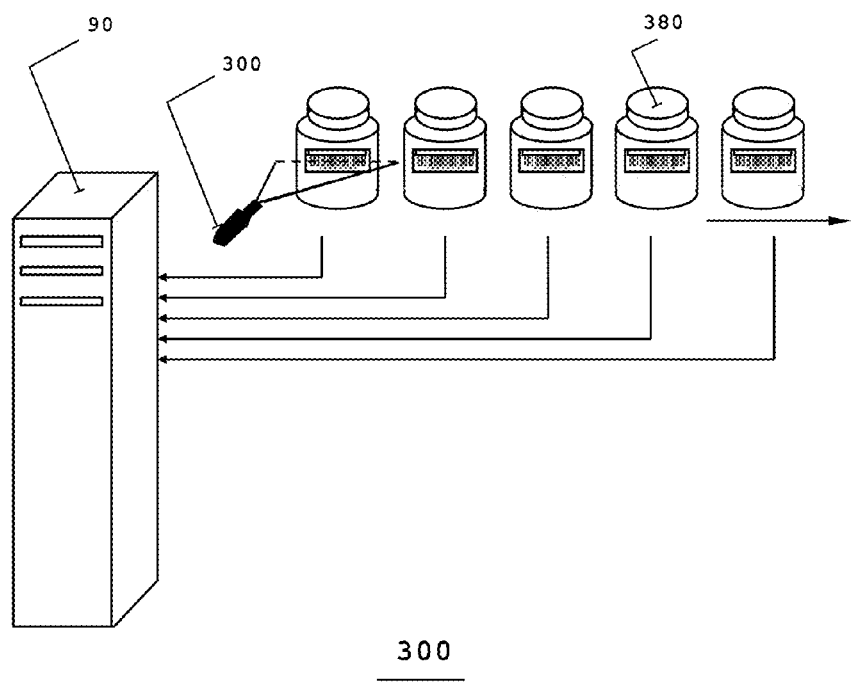
Figure 11.2, A Schematic Diagram of the Work Station Control Encoding the Exiting Product with a Barcode Device

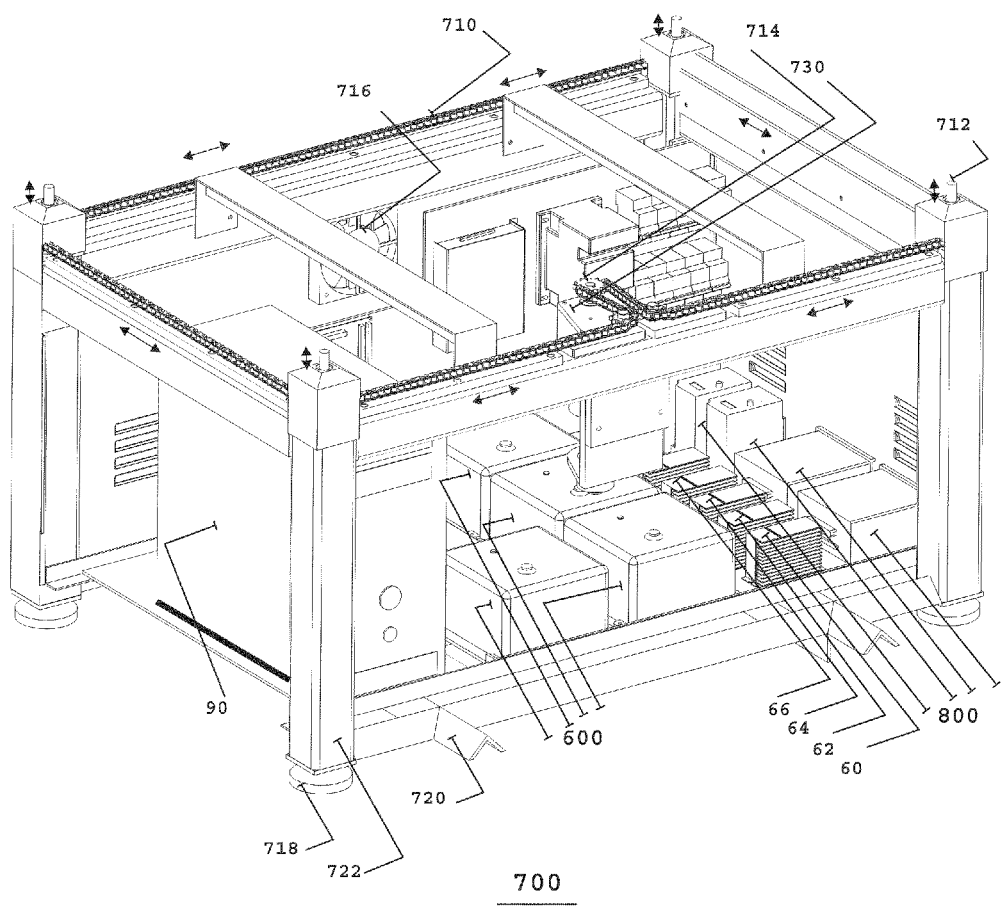
Figure 12, A Perspective View of the Structural Support Base of the Invention, and the Lower Compartment of the Invention Containing the Programmable Logic Controller, as well as the Work-Station Analysis and Control System Figure 13.1 Present Invention Flowchart 1 of 6
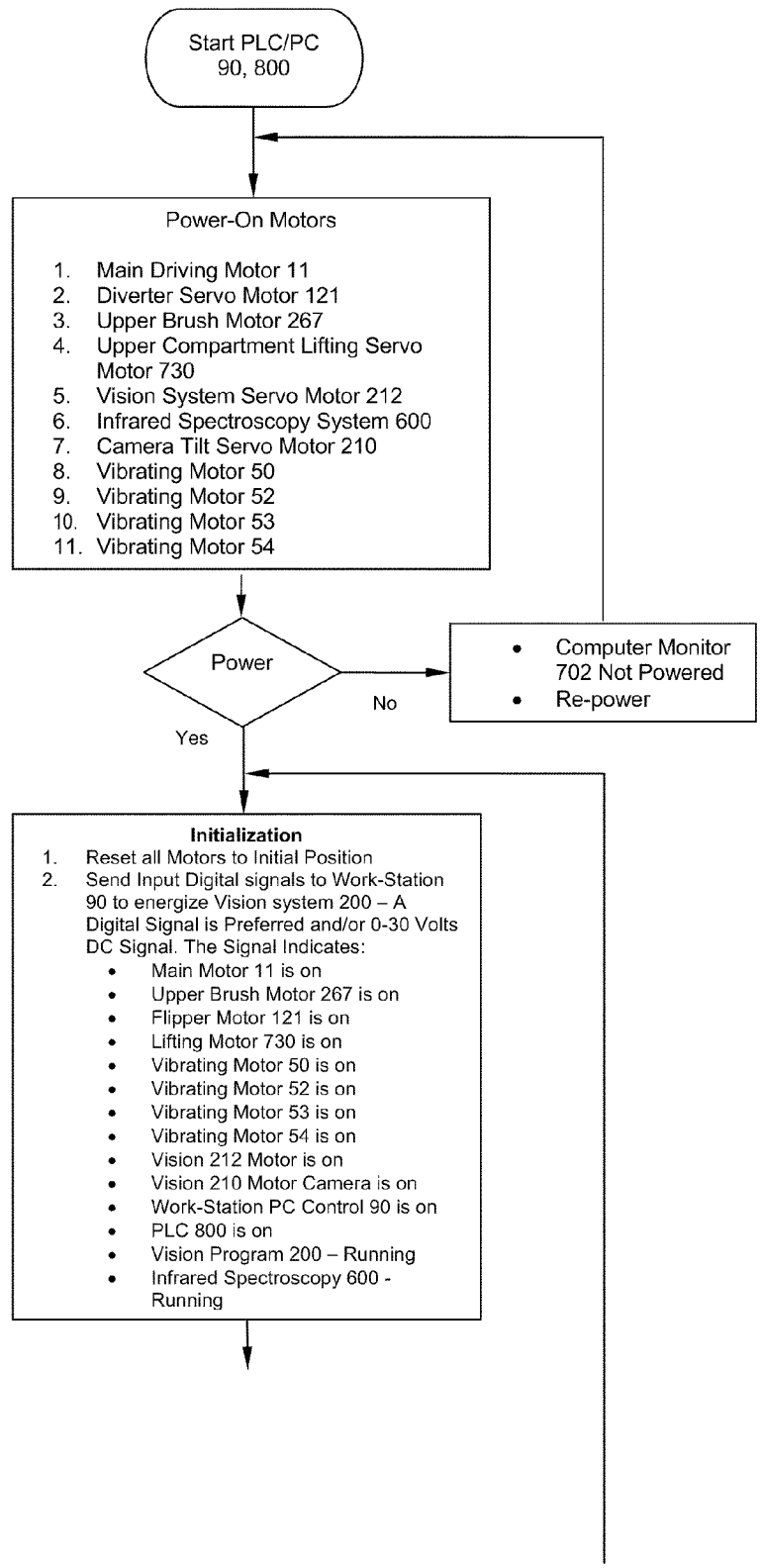

Figure 13.2 Present Invention Flowchart - Continue 2 of 6
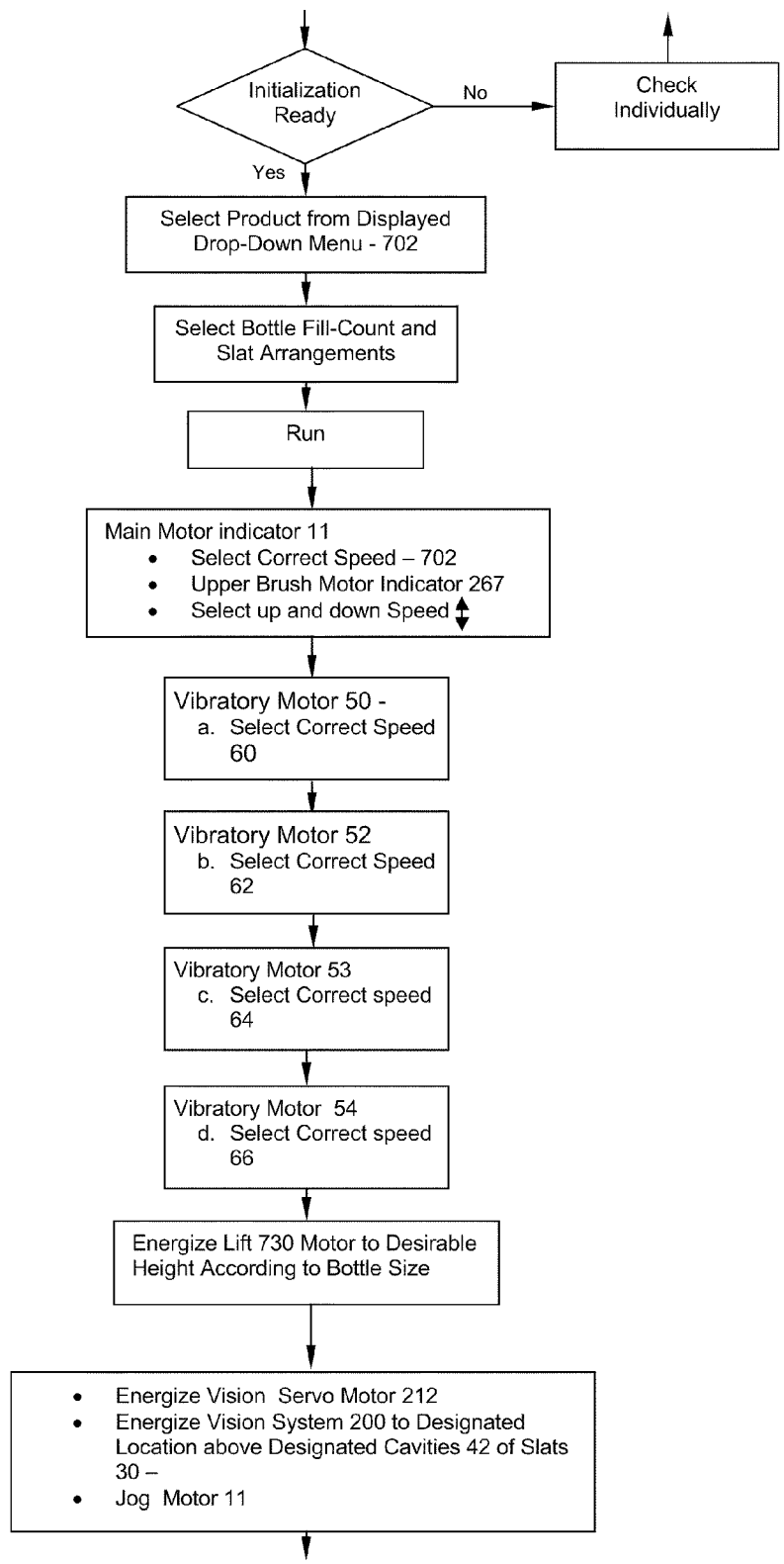

Figure 13.3 Present Invention Flowchart - Continue 3 of 6
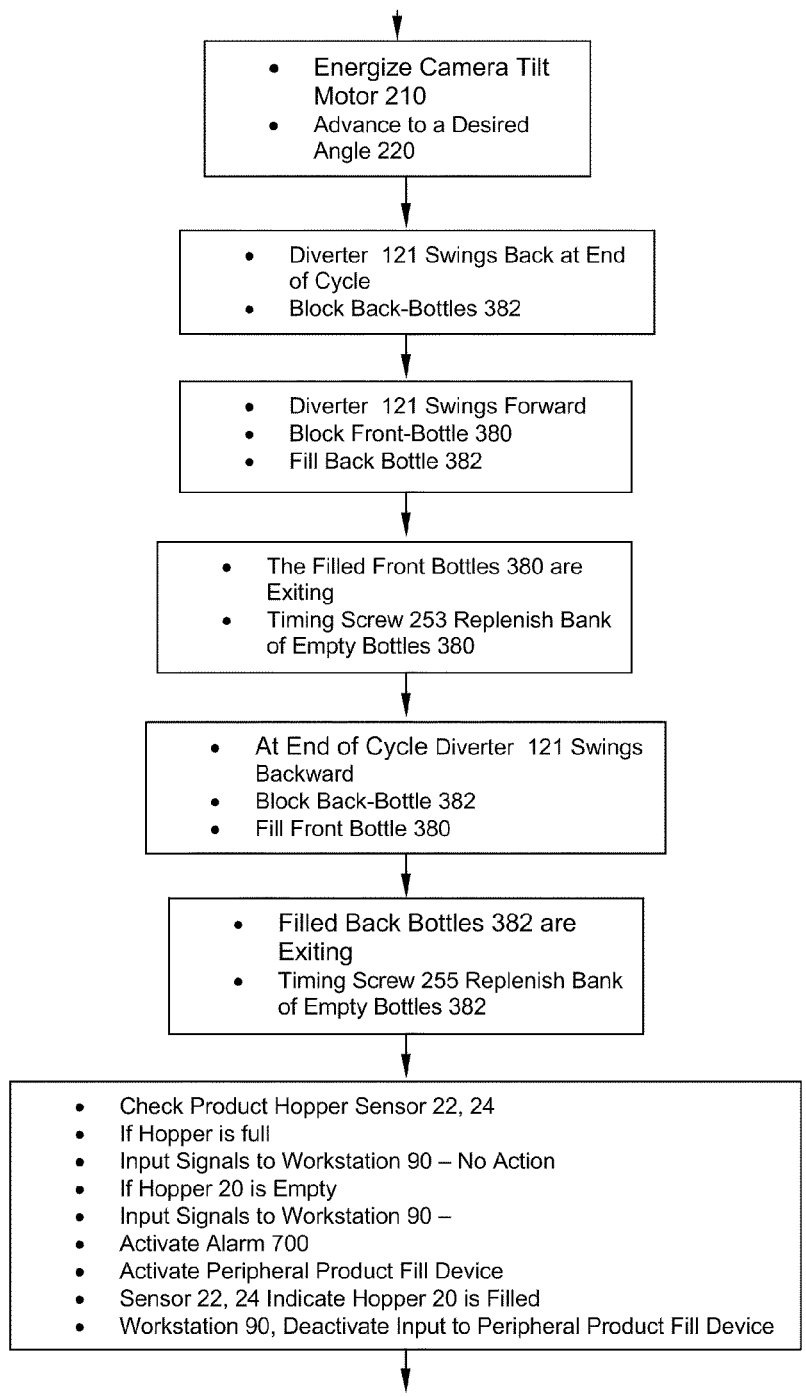

Figure 13.4 Present Invention Flowchart - Continue 4 of 6
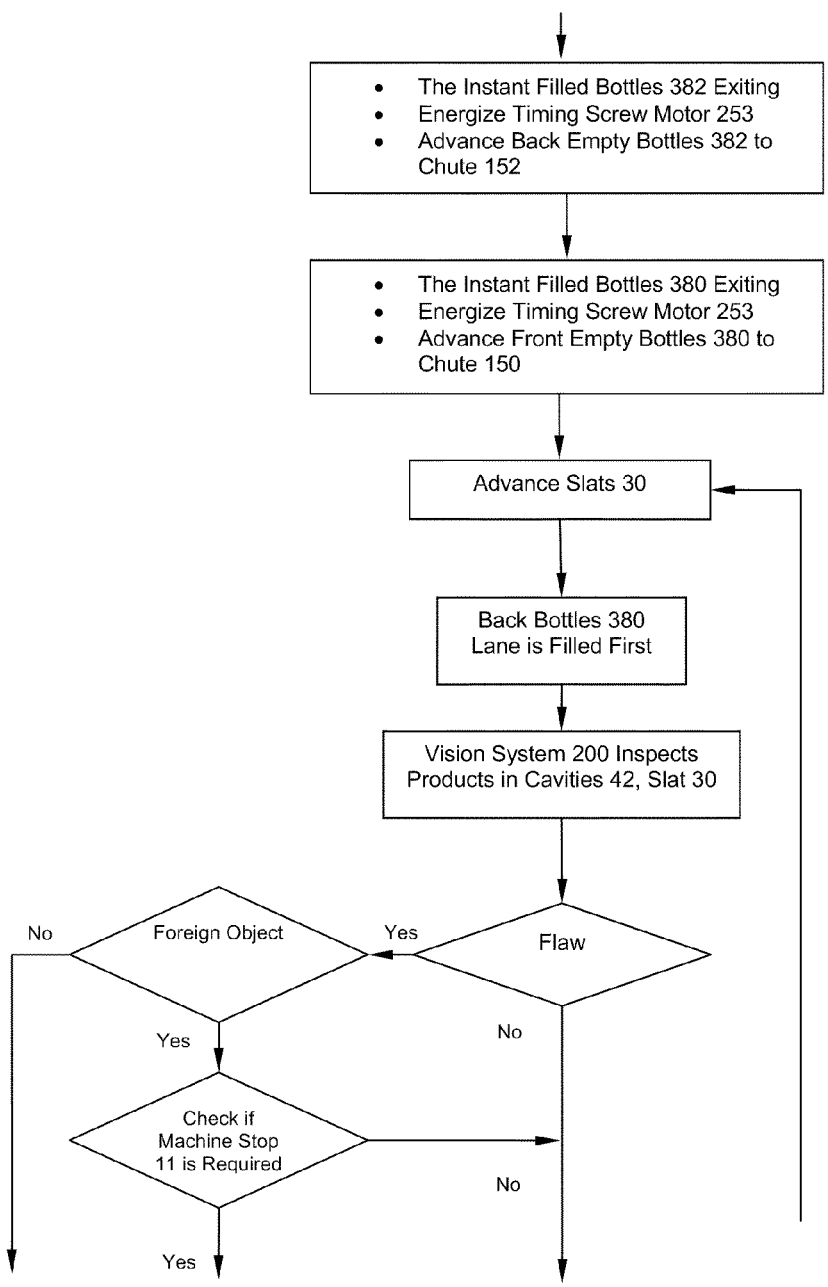

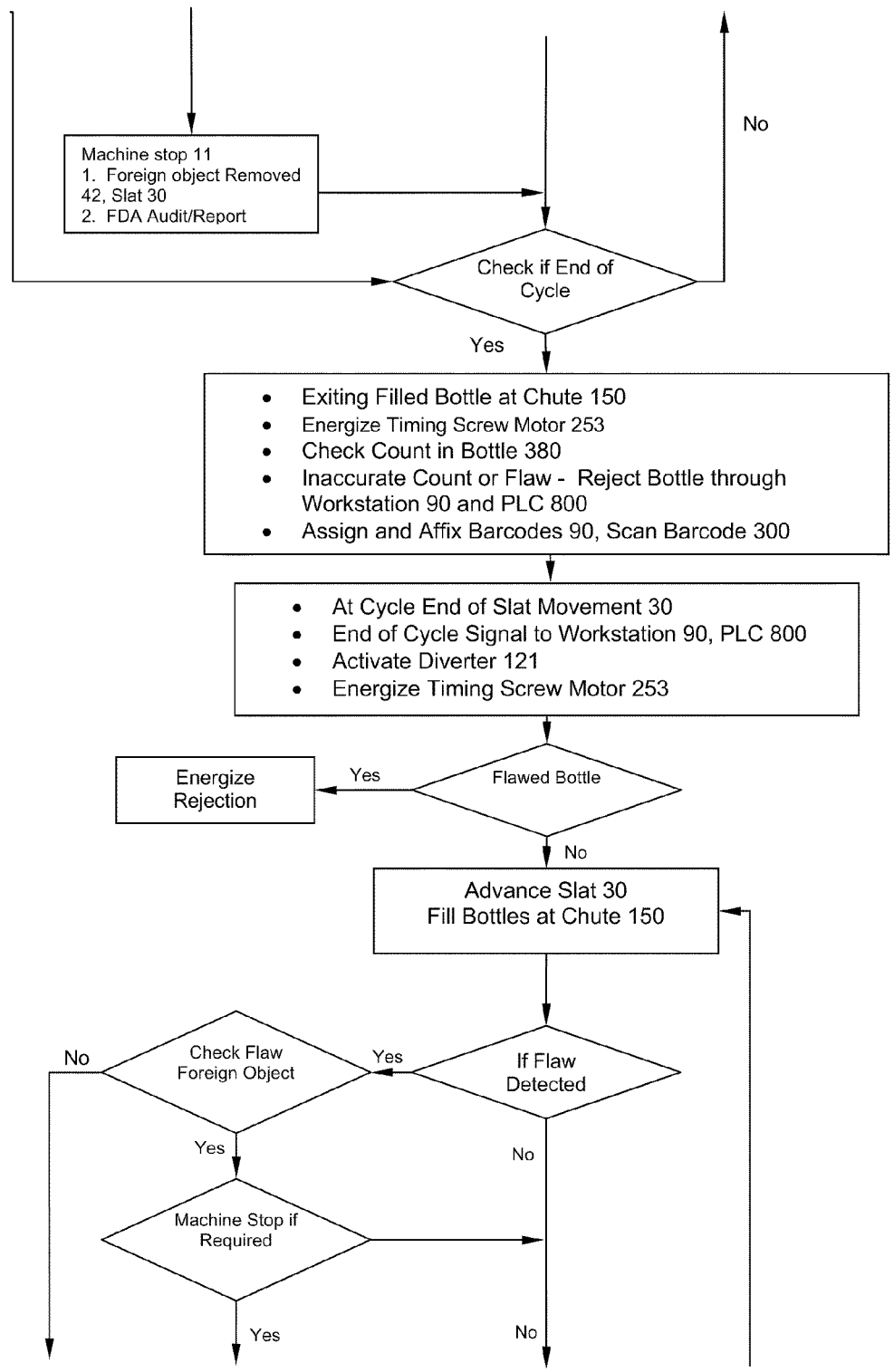
Figure 13.5 Patent Flow Chart - Continue 5 of 6

Figure 13.6 Patent Flow Chart - Continue 6 of 6
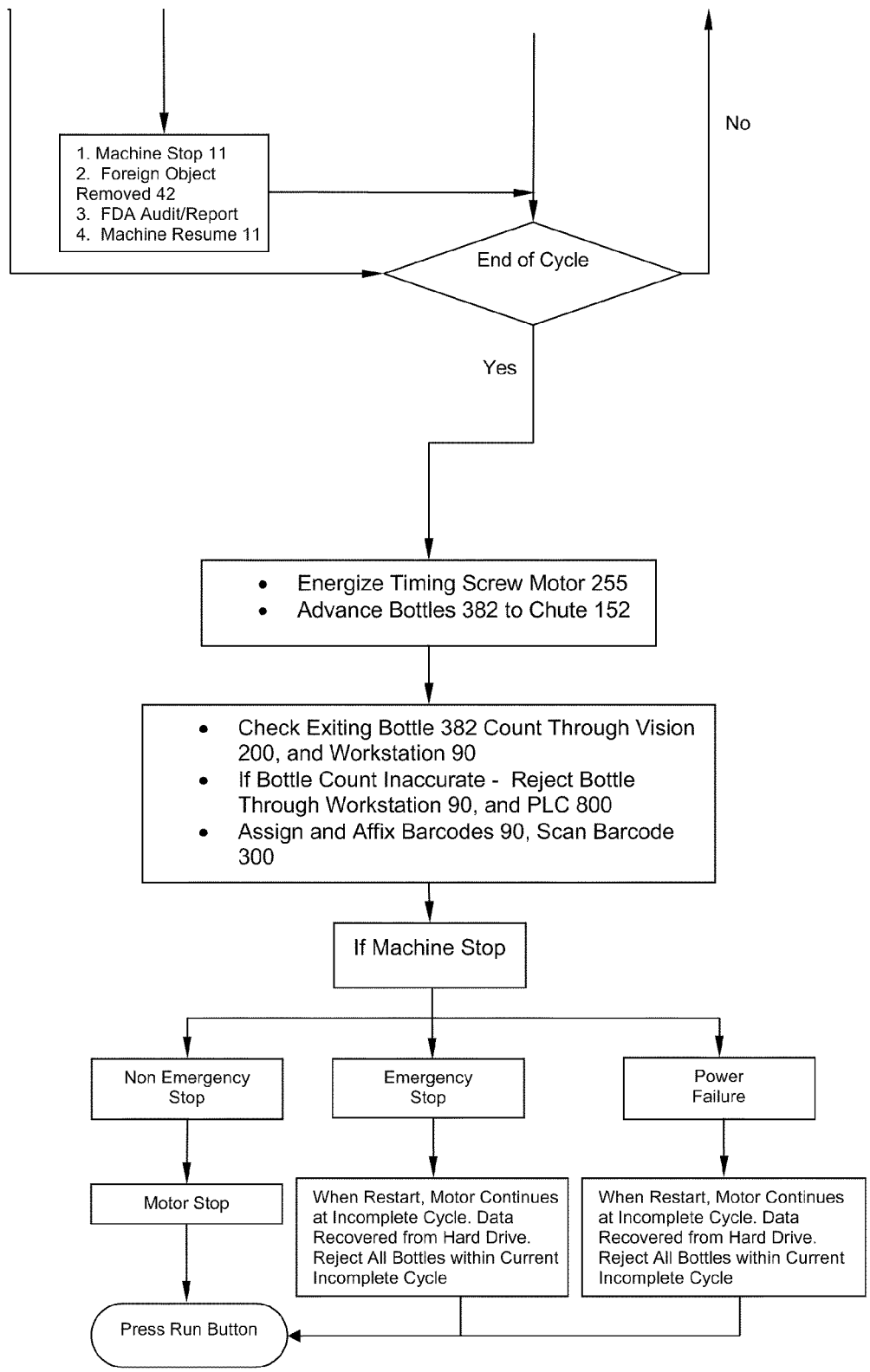

AUTOMATED PACKAGING, INSPECTION, VERIFICATION, AND COUNTING APPARATUS

CROSS-REFERENCE TO RELATED APPLICATIONS (Not Applicable.)

STATEMENT REGARDING FEDERALLY SPONSORED RESEARCH AND DEVELOPMENT (Not Applicable.)

FIELD OF THE INVENTION

This invention relates to packaging machines, and more particularly to automated packaging machines utilized for inspecting, counting, and verification of the physical and chemical composition of discrete pharmaceutical, vitamin, or food products such as tablets or capsules, and packaging them in containers.

DISCUSSION OF RELATED ART

Pharmaceutical industries require automated packaging apparatus to count, inspect and package predetermined quantities of discrete dosage items such as capsules and tablets. These products must be manufactured, inspected, counted, and their active ingredients measured by weight. The products must be packaged in containers in accordance with strict Federal regulations, including exactly meeting the product count and information labeled on the containers, and insuring the correct chemical composition of the products. Several prior art devices are known which provide automated packaging of discrete pharmaceutical products. U.S. Pat. No. 6,799,413 to Aylward discloses an automated packaging apparatus including a plurality of independently rotatable slats containing tablet, capsule, or gel apertures. Open product containers move along a conveyor adjacent to the slats so that tablets are dispensed into the containers. A delivery sensor and controller are used to determine when a corresponding container is filled.

U.S. Pat. No. 4,674,259 to Hills provides a container filling machine including a plurality of elongated slats with cavities which dispense tablets or capsules into a set of chutes. A reciprocating mechanism drives the chutes to dispense tablets or capsules between the first and second rows of containers positioned at the filling station. To insure an accurate count of products in each container, an operator may be situated adjacent to the slats who must insure that each container is correctly filled. This method has several drawbacks including labor costs, the possibility of human error, and possible sterility problems.

Insuring the exact accuracy of the claimed product count, high chemical purity, and the exact amount of active ingredients of the dispensed products is a paramount requirement in pharmaceutical packaging equipment. The various systems employed in the prior art to insure accuracy of the product count, and to insure the chemical composition of the products, are inadequate when compared to a system which utilizes digital computer and spectroscopy technologies to accomplish those objectives.

Clearly there is a need for an automated packaging apparatus which accurately analyzes, records, and counts the contents of each filled container. Such a system would operate at high speed, require either minimum or no operator intervention, and would utilize digital computer and spectroscopy technologies to record and analyze product data during the packaging process. The present invention accomplishes these objectives.

SUMMARY OF THE INVENTION

The present invention is directed to an automated inspection, chemical measurement and verification, counting and packaging apparatus for dispensing discrete pharmaceutical, vitamin, or food products into various types of empty containers moving on a conveyor belt, including but not limited to bottles, jars, boxes, and the like. These discrete products may comprise but are not limited to tablets, capsules, caplets, gels, vitamins, and the like.

The automated inspection, chemical verification, counting and packaging apparatus includes a main hopper, a plurality of elongated slats which rotate in unison, and a bottom cabinet containing a computerized analysis system and a spectroscopy processing system. Discrete pharmaceutical, vitamin, or food products ready for packaging are deposited into the main hopper. Each slat contains a plurality of cylindrical cavities to receive and dispense the pharmaceutical, vitamin, or food products. A drive system is comprised of one or more drive motors connected to a plurality of drive chains and gears. The slats rotate in unison at speeds determined by the speed of the drive motors. Motors equipped with servo motor devices control the slat displacements at any given instant.

The invention includes a vision inspection system which inspects and counts the pharmaceutical, vitamin, or food products before they are dispensed into their containers, while simultaneously electronically recording the status of each pharmaceutical, vitamin, or food product. Appropriate alerts are produced by the alerting system if error conditions are detected by the vision inspection and/or by the spectroscopy system.

An automated non-destructive real time spectroscopy system measures and inspects the chemical composition of the discrete products by weight before they are dispensed into their containers while electronically recording the status of each product. Appropriate alerts are produced by the alerting system if error conditions are detected by the spectroscopy system.

The sequence of motions of the various components of the apparatus are controlled by a PLC (programmable logic controller). A bar code reader is configured to scan the affixed bar code on each container, so that the data recorded by the analysis system is correlated with each container, thereby insuring the safety of consumers utilizing said products.

During operation of the automated packaging apparatus, each empty container receives a predetermined quality and quantity of pharmaceutical, vitamin, or food products. The automated packaging apparatus achieves a high container filling speed by allowing the slats to rotate continuously without slowing or stopping. A two tiered, parallel dispensing manifold allows a continuous flow of discrete products into the empty containers traveling on the conveyor belt.

Other features and advantages of the present invention will become apparent from the following more detailed description, taken in conjunction with the accompanying drawings, which illustrate, by way of example, the principles of the invention.

DESCRIPTION OF THE DRAWINGS

FIG. 1 is a front perspective view of the invention, illustrating an automated packaging apparatus;

FIG. 1.1 is a Perspective View of the Upper Part of the Apparatus Illustrating Vibrating Motors, and Upper and Lower Brush Mechanisms;

FIG. 1.2 is a Perspective View of the Lower Part of the Apparatus illustrating the Base Structure, PLC Control, Workstation PC Control, Spectroscopy, and Lift Mechanisms;

FIG. 1.3 is a Perspective View of the Apparatus Illustrating the Automatic Vision Inspection System;

FIG. 2 is a rear perspective view of the invention, illustrating an automated packaging apparatus;

FIG. 3 is a left side view of the invention, illustrating the drive mechanism of the present invention;

FIG. 4 are Perspective Views Illustrating a Slat with Cavities, and its Corresponding Engaging Pins of the Present Invention;

FIG. 4.1 is a Perspective View Illustrating the Synchronized Motion of a Slat Empty of Products;

FIG. 5 is a Close up Perspective View of the Invention, Illustrating the Rake Assembly and its Relative Location in the Present Invention;

FIG. 6 is a close-up perspective view of the invention, illustrating the Divider Assembly of the Present Invention;

FIG. 6.1 is a Close up Perspective View of the Invention, Illustrating the Divider Assembly Configured with the Diverter Assembly of the Present Invention;

FIG. 7 is a Close-up Perspective View of the Invention, Illustrating the Dispenser Assembly of the Present Invention;

FIG. 7.1 is a Close up View of the Invention, Illustrating the Location of Products Exiting the Dispenser Assembly of the Present Invention;

FIG. 8 is a Close-up perspective View of the Invention, Illustrating the Vision Inspection System of the Present Invention;

FIG. 8.1 is a Perspective View Illustrating the Linear Drive Mechanism of the Vision Inspection System of the Present Invention;

FIG. 8.2 is a Perspective View Illustrating the Rotational Drive Mechanism of the Vision Inspection System of the Present Invention;

FIG. 9 is a close up Schematic Diagram of the Invention, Illustrating the Spectroscopy System of the Present Invention;

FIG. 9.1 is a perspective View of the Invention, Illustrating the Spectroscopy Probes to Convey and Receive Infrared Energies;

FIG. 10.1 is a Perspective View of the Present Invention, Illustrating the Upper Brush Assembly;

FIG. 10.2 is A Close-Up Perspective View of the Present Invention, Illustrating the Lower Brush Assembly;

FIG. 11 are perspective views of the Lower Compartment of the Present Invention and the Upper Compartment of the Present Invention;

FIG. 11.1 is a Schematic Illustration of the Timing Screw Mechanism of the Present Invention;

FIG. 11.2 is a Schematic Diagram of the Apparatus Work Station Controller Encoding the Exiting Product with a Barcode Device;

FIG. 12 is a Perspective View of the Structural Support Base of the Invention, and the Lower Compartment of the Invention Containing the Programmable Logic Controller as well as the Work Station Analysis and Control System;

FIG. 13.1 is Part 1 of 6 Parts of a Collective Flow-Chart of the Present Invention Describing Sequential Steps to Start PLC/PC 90, 800 as well as Starting all System Driving Components and Inspection Systems Including the Infrared Spectroscopy Analytical System 600;

FIG. 13.2 is Part 2 of 6 Parts of a Collective Flow-Chart of the Present Invention Describing the Initialization Sequence of the System Driving Components, and Selecting Specific Product for Packaging, Counting, Verification, Inspection, and Analysis, as well as a Sequence for Initializing the Main Motor 11 for a Jog Mode Function;

FIG. 13.3 is Part 3 of 6 Parts of a Collective Flow-Chart of the Present Invention Stating Sequential Steps to Energize the Camera Tilt Motor 210 until the Activation Steps to Fill Hopper 20;

FIG. 13.4 is Part 4 of 6 Parts of a Collective Flow-Chart of the Present Invention Stating Sequential Steps of Filled Exiting Bottle 382 to Steps Ensuring Vision System 200 Verifies if Main Machine Motor 11 Must Stop as a Consequence of the Presence of a Foreign Product Representing a Fatal-Flaw, or Machine May Continue if the Flaw is Representing a Process-Flaw, which will be Rejected at a Later Instant;

FIG. 13.5 is Part 5 of 6 Parts of a Collective Flow-Chart of the Present Invention Stating Sequential Steps of Stopping the Machine to Conduct an FDA Audit/Report in Case of Detection of a Foreign Product Representing a Fatal-Flaw Product;

FIG. 13.6 is Part 6 of 6 Parts of a Collective Flow-Chart of the Present Invention Stating Sequential Steps of Removing Unwanted Foreign Object 42 to Steps of Restarting Machine Motor 11 Again.

DETAILED DESCRIPTION OF THE PREFERRED EMBODIMENT

The present invention will now be described more fully with reference to the accompanying figures. Although the accompanying figures show preferred embodiments of the invention, the invention may be embodied in many different forms and should not be construed as limited to the embodiments described herein.

The present invention is directed to an automated packaging apparatus 10 for dispensing discrete pharmaceutical, vitamin, or food products into various types of empty containers moving on a conveyor belt, including but not limited to bottles, jars, boxes, etc. These discrete products may comprise but are not limited to tablets, capsules, caplets, vitamins, etc.

As shown in FIGS. 1, 1.1, 1.2, and 1.3, the automated packaging apparatus 10 includes the main hopper 20, a plurality of elongated slats 30, the bottom cabinet 70, the vibrating motors 50, 52, 53, 54, the camera tilt motor 210, the Encoder 220, and the drive chain 100.

Pharmaceutical, vitamin, or food products ready for packaging are deposited into the main hopper 20 of the packaging apparatus 10. An outlet from the main hopper 20 conveys the pharmaceutical, vitamin, or food products into a plurality of elongated slats 30 comprised of FDA approved material.

Turning to FIGS. 4 and 4.1 we are shown a detailed view of a linear elongated slat 30. Each slat 30 contains a plurality of cylindrical bifurcated cavities 42, each cavity divided by a gap 48. Each cavity contains apertures 40 in the shape of curved channels within the cavities 42 to receive and dispense pharmaceutical, vitamin, or food products. Each slat 30 is reinforced by a slat reinforcement 44 containing a tee shaped alignment 46 on its bottom which enters a grooved wheel 45 to stabilize the slat 30 at appropriate moments while the slat assembly is being rotated by the drive system. The ends of each slat 30 are constructed with pin holes 21, 23 which precisely fit the pins 25,27 located at each attached chain link 102, 104.

Returning to FIGS. 1 and 1.3, a product distribution system includes a plurality of vibrating motors 50,52,53,54, configured in four different locations, and activated by one or more level sensors 22, 24. The level sensors 22, 24 detect the presence of pharmaceutical, vitamin, or food products within the hopper 20. The action of the vibrating motors 50,52,53,54 causes the pharmaceutical, vitamin, or food products to be evenly distributed within the cavities 42 of the entire slats 30 located adjacent to the outlet of the hopper 20. The vibrating motors 50,52,53,54 are controlled by four separate circuits 60, 62, 64, 66 which adjust the amplitude of the motor vibrations and their corresponding frequencies.

In FIGS. 2 and 3 is shown the drive system, comprised of one or more drive motors 11 connected to a plurality of drive chains 102,104 and to a plurality of gears 301,303,305. Each end 21,23 of each slat 30 is connected to drive chains 102,104 whose tension may be adjusted thereby preventing the drive chains 102,104 from sagging. The drive motors 11 are rotatable at different speeds, so that the slats 30 rotate in unison at speeds determined by the speed of the drive motors 11. The tension of the main drive chains can be easily adjusted to enable optimum and efficient packaging operation.

In FIGS. 1, 1.3 and 3 are shown the vision inspection system 200, whose function is to physically inspect and count the pharmaceutical, vitamin, or food products. The vision inspection system 200 is comprised of a cluster of cameras 211 installed in a special compartment equipped with a plurality of motors 212 and servo motors 210 which enable the cluster of cameras 211 to advance, retract or tilt, thus providing maximum visibility of the products passing the cameras' 211 field of views. The servo motor/encoder 210 synchronize the capture of data when the pharmaceutical, vitamin, or food products are in the correct proximity to the vision inspection system 200. Each camera 211 is designated to acquire the data captured in either Chromatic light variations of Black-White and Grey or else in combinations of Red, Green, and Blue light elements. Each camera 211 thereby inspects a specific number of cavities 42 to determine if they are filled with products or empty. Each camera 211 within the cluster of the vision inspection system 200 also identifies many types of visible product flaws such as incorrect colors, incorrect dimensions, incorrect color combinations, color bands around each product, deformed products, dirty products, cracked products, exploded products, broken products, and the like.

During operation of the invention, while the products are passing the camera 211 field of view, the vision inspection system 200 counts the total number of products within each specific group of slats 30 and mathematically compares the actual accumulated total to the correct count designated for each corresponding bottle. If an error or flaw is detected by the vision inspection system 200 within the total number of accumulated products in a certain group of slat 30 segments, that group is rejected and the container is redirected to a special type of reject chute depending on the type of flaw. Containers with less than the correct predetermined count are deemed unacceptable, and thus rejected. Detection of a fatal foreign product or object by the vision inspection system 200 results in an instant and complete stop to the entire machine. The vision inspection system 200 will guide the administrator to the exact location of the detected fatal error in a certain cavity. A series of FDA procedural protocols automatically appears on the display screen. Each production step has to be completed by an authorized individual who possesses the correct password. The correct password enables the machine to be unlocked once the fatal error is removed and placed in a quarantined location.

In FIGS. 9 and 9.1 are illustrated the real time spectroscopy system 600, which measures and inspects the chemical composition of the pharmaceutical, vitamin, or food products before they are dispensed into their containers. The real time spectroscopy system 600 includes a bundle of fiber optics probes 601 properly situated to focus and transmit infrared light waves on the passing tablets, capsules, gels, and organic-base compounds. The fiber optic probes 102 then receive the reflected infrared light waves from the same. The fiber optic probes 601 and 602 are placed at an optimum distance from the passing products. The optimum distance is automatically determined by the spectroscopy system allowing the exact optical distance to be maintained regardless of the shape and configuration of the passing products. The probe 602 which is receiving reflected infrared energies is directly linked to the spectrophotometer 600 to obtain the corresponding spectrum of each product passing under the combined sending and receiving fiber optic probes 601 and 602. A succession of collimated beams throughout the middle and near infrared spectrum are transmitted through the fiber optic probes 602 located above each product in the slat 30 cavity 42. The collimated beams are impinged against a sample or samples and the diffused component of the reflected light is measured throughout the spectrum. This diffuse component is analyzed by several algorithms including neural network methodologies to determine such characteristics as the contents and the active ingredients of the passing product.

The spectrophotometer 600 transmits data to a high performance workstation analysis system 90 which determines the exact chemical composition of solid and non-solid organic-base compounds. Also determined by the workstation analysis system 90 is the dissolution measurement as well as the hardness of each manufactured solid organic-base compound.

Product data produced by the vision inspection system 200 and the spectroscopy system 600 are transmitted to a workstation analysis system 90, installed in the bottom cabinet 70 of the apparatus 10 (FIGS. 1, 8.2, 9, and 12). The workstation analysis system 90 is a high performance workstation computer system and associated arithmetic circuits, a storage system for storing and retrieving data on a storage medium, a computer operating system, and a method of using the workstation computer system 90 to record and analyze data. The workstation analysis system 90 continually processes and records product data produced by the vision inspection system 200 and spectroscopy system 600, including the status of each discrete product. The alerting system 700 is thereby activated in response to product quality and quantity conditions detected.

The sequence of motions of the various components of the apparatus including the drive system motors 11, conveyor belts, rejection mechanisms, and the like are controlled by a PLC (programmable logic controller) 800 and its associated logic circuits and relays installed in the bottom cabinet 70 of the apparatus (FIGS. 1, 11, and 12).

During operation of the apparatus the slats 30 are rotating continuously, and at specific moments the slat cavities 42 are turned almost upside down (FIG. 4.1). The discrete products previously deposited inside the slat cavities 42 then fall into a divider assembly 110. In FIGS. 4, 6, and 6.1 are shown the divider assembly 110 containing a predetermined number of divider plates 112 comprised of contoured partitions 113 shaped to accommodate the movements of the slats 30. The contoured partitions 113 are configured to allow certain slat peak areas 49 to rotate very close to the edges of the contoured partitions 113, thereby trapping a certain number of cavities and enabling the corresponding products to fall from their cylindrical contoured channels 40 of slat 30 into the divider assembly 110. Within the divider assembly 110 is a divider dispensing compartment 118 and a diverter assembly 120 containing diverter controls 121. A set of diverters 120 are configured directly at the bottom of the divider assembly 110. The diverters 120 are activated at the correct instants to cause the discrete products to be conveyed to either set of front cups 130 or set of rear cups 132 in the dispenser assembly (FIG. 7). The containers themselves are arranged in a plurality of tiers beneath the manifold 140,142 in order to receive the products being deposited into them through a plurality of chute tiers 150, 152.

Turning now to FIGS. 7 and 7.1, pharmaceutical, vitamin, or food products are conveyed by the divider assembly 110 into a dispenser assembly 115 which leads to a front manifold 140 containing front cups 130 and a rear manifold 142 containing rear cups 132. The front and rear cups 130, 132 connect to front and rear dispensing chutes 150, 152 arranged in two tiers. The manifolds 140, 142 define a plurality of delivery paths for the pharmaceutical, vitamin, or food products into the containers being conveyed below the manifolds 140, 142.

In FIG. 5 is shown a rake assembly 160 containing a plurality of parallel rake blades 162. During rotation of the slats 30, and after the discrete products have fallen out of the slat cavities 42, the rake assembly 160 enters the slat gap 48. The equally spaced rake blades 162 within the rake assembly 160 enter the gaps 48 within the slat cavities 42 and thereby expel any discrete pharmaceutical, vitamin, or food products which remain within the slat cavities 42. The contour of the rake blades 162 are designed specifically to allow the rake blades 162 to smoothly slide next to the fragile discrete products, and dislodge them. The thickness of the rake blades 162 are directly correlated with the minimum dimensions of the discrete products within the slat cavities 42, so that each product can be dislodged without being damaged.

Turning to FIGS. 10.1 and 10.2, detail of the upper brush assembly 267 and lower brush assembly 265 are illustrated. The upper brush assembly 267 insures that only a single or predetermined multiple quantity of products enter the cavities 42 when the products are flooding the cavities 42. The lower brush assembly 265 insures that none of the debris or broken products remain in the cavities 42 after the cavities 42 are emptied of products. The lower brush assembly 265 also removes dirt and cleans discolored slats 30 and cavities 42.

In one embodiment of the invention, the apparatus contains a total of 72 elongated slats 30, each slat 30 containing eighty cavities 42, where each cavity 42 holds one discrete pharmaceutical, vitamin, or food product. Within the divider assembly 110 are 20 divider plates 112. Each divider plate 112 then receives four discrete products which are conveyed into one dispensing chute 150,152 within the dispenser assembly 115 (FIGS. 7 and 7.1).

Turning to FIG. 11.1, 4, and 4.1, the bottle transporting and timing system includes a timing screw 252, a timing screw drive 253, and a plurality of synchronizing wheels 32, 34, 45, synchronized pins 25, 27 corresponding with slat positioning holes 21, 23 which insure that the packaging apparatus dispenses the pharmaceutical, vitamin, or food products into the containers when the containers are correctly positioned to receive the pharmaceutical, vitamin, or food products. The timing screw servo motors 253, 255 automatically activate timing screws 252, 254 at the correct moment to allow a set of filled containers to depart to the accept-reject station. The same timing screw 252, 254 then cause a fresh set of empty containers to be conveyed beneath the dispensing chutes 150, 152. The timing screws 252, 254 then stop while this new set of containers are filled with pharmaceutical, vitamin, or food products As each container 380, 382 is filled with the correct number of discrete products, the computer system 90 transmits a signal to the servo motor encoder 121 of the diverter 120 thereby blocking the further path of products into that tier of containers (FIGS. 6 and 6.1). Products can then be directed to the other tier of empty containers (FIG. 11.1).

A bar code reader 300 is configured to scan the affixed bar code on each container, so that the data generated by the vision inspection system 200 and the spectroscopy system 600 are recorded by the workstation analysis system 90 and are correlated with each container, including correlating the product data and date and time stamps of the pharmaceutical, vitamin, or food products, and thereby insuring the safety of consumers utilizing said products (FIG. 11.2).

The alerting system 700 produces visual and audio alarms indicating various conditions of the apparatus including powering up, normal operation, and fault conditions, and also alerts the apparatus operator when foreign, chemically deviated, or incorrect products are detected (FIG. 1).

A control panel 702 (FIG. 4) allows the operator to control the operation of the apparatus.

Turning to FIG. 12, the structural frame support 700 of the packaging machine constitutes a base support to the upper compartment of the system and contains the Programmable Logic Controller 800, the work station controller 90, the spectroscopy infrared identification and verification system 600, and vibrating motors controller, 60, 62, 64, and 66. The structural support 700 is constructed of High Strength Stainless Steel material equipped to accommodate static and dynamic loads placed above its frames.

The structural base Support 700 contains a lift motor 730 with a gear reducer to decrease its rotating speed. The end shaft of the motor 730 is fitted with a driving gear 714. The driving gear 714 is fitted with an endless loop chain 710. The endless loop chain 710 is wrapped around 4 lead screws 712 placed inside the four supporting legs of base structure 700.

The Work-Station Controller 90 sends a command to the PLC controller 800 to rotate the motor 730 clockwise or counter clockwise, and consequently rotates the four lead screws 712 through its endless loop chain 710 either upward or downwards, thereby lifting up or lowering the upper compartment of the apparatus 71. Once the operator selects the intended product through the display monitor 702, the upper compartment of the apparatus 71 is lifted up to a specific predetermined distance encoded in the routines of the selected product for packaging, counting, inspection, and chemical composition identification and verification analysis.

If another product is selected by the operator the Work-Station controller 90 automatically directs the spectroscopy infrared system 600 to the predetermined routine, and the vision system 200 to rotates its cameras 211 a certain number of degrees using its motor 212 and its encoder 210. The work station controller 90 then moves in a linear motion forward or backward the entire vision system 200 to a specific location encoded in the selected product routine (FIGS. 8, 8.1, and 8.2). The linear motion of vision system 200 is parallel to the slats 30. Once the selected product code through the drop down menu is displayed on monitor 702, the four lead screws 712 will be automatically activated to raise or lower the upper compartment 71.

During operation of the automated packaging apparatus 10, the pharmaceutical, vitamin, or food products are conveyed from the hopper 20 into the cavities 42 of the rotating slats 30. The products are then released from the cavities 42 and conveyed through the divider assembly 110, and then conveyed through the dispenser assembly 115 into the manifold 140, 142, through chutes 150, 152 and then into the containers being conveyed near the packaging apparatus 10. Each container thereby receives a predetermined quality and quantity of pharmaceutical, vitamin, or food products.

The automated packaging apparatus 10 achieves a high container filling speed by allowing the slats 30 to rotate continuously without slowing or stopping. The two tiered dispensing chutes 150, 152 allow a continuous flow of discrete products into the empty containers traveling on the conveyor belt. Once the containers under one dispensing tier are filled correctly, the diverter 120 is energized so that the containers within the other tier can be filled with products (FIGS. 6 and 6.1).

The packaging system will shut down the entire operation when a foreign product is detected preventing a foreign product from reaching the container that may harm the end user and may even cause death. The presence of a foreign product may cause the loss of the production license to manufacture, package, and distribute such product according to FDA regulations. The vision system will pin point the presence of a detected flaw or unwanted foreign product to the exact location in the slat much before it reaches the final destination of the container. The machine is not permitted to resume operation until the unwanted foreign product is removed thereby allowing strict enforcement of CFR-21 Part-11 rules according to the FDA's GMP (good manufacturing protocols).

While a particular form of the invention has been illustrated and described, it will be apparent that various modifications can be made without departing from the spirit and scope of the invention. For example, the quantity of slats or slat cavities could be adjusted to various values. Accordingly, it is not intended that the invention be limited, except as by the appended claims.

That which is claimed is:

1. An automated packaging apparatus comprising:
   a reservoir configured to receive discrete product units;
   a drive system;
   a plurality of rotating linear elongated slats attached to said drive system, each slat having a proximal end and a distal end;
   a plurality of cavities arranged along the longitudinal axis of each said slat, wherein each cavity is bifurcated by a channel passing through the cavity;
   rake blade means for raking said channels in the bifurcated cavities and expelling all objects;
   a control system;
   a divider assembly;
   a dispenser assembly comprised of a plurality of manifolds connected to chutes configured to dispense predetermined quantities of discrete product units into containers moving proximate to the packaging apparatus.

2. The automated packaging apparatus of claim 1 further comprising a plurality of level sensors for detecting the presence of product units in the hopper, a plurality of vibrating motors activated by the level sensors, and circuits which adjust the motor vibrations, whereby product units may be distributed within the hopper.

3. The automated packaging apparatus of claim 1 wherein the aperture of each said cavity is curved to facilitate the receiving and dispensing of discrete product units.

4. The automated packaging apparatus of claim 1 wherein said control system further includes a PLC (programmable logic controller) and associated logic circuits and relays to control the various components of the apparatus including said drive system.

5. The automated packaging apparatus of claim 1 wherein said divider assembly comprises:
   a plurality of adjacent contoured divider plates, each divider plate configured to convey a predetermined quantity of discrete products;
   a plurality of diverters proximate to the divider plates configured to convey groups of discrete products to specific tiers in said dispenser assembly;
   a diverter control assembly;
   whereby discrete product units are conveyed from the bifurcated cavities into said dispenser assembly.

6. The automated packaging apparatus of claim 1 wherein said dispenser assembly comprises:
   a plurality of manifolds, wherein each manifold is comprised of a plurality of adjacent funnel shaped cups arranged in a linear tier;
   a plurality of linear chute tiers, wherein each chute tier is comprised of a plurality of adjacent chutes, each chute connected to the outlet of a said funnel shaped cup;
   whereby discrete product units are conveyed into containers moving proximate to the outlets of the chute tiers.

7. The automated packaging apparatus of claim 1 wherein each said slat is comprised of FDA approved material.

8. The automated packaging apparatus of claim 1 further including a timing system comprising:
   a plurality of timing screws;
   a plurality of timing screw drives;
   a plurality of servo-motors connected to said timing screws;
   a plurality of electronic encoders connected to said timing screws;
   a plurality of synchronizing wheels;
   a plurality of synchronizing pins;
   whereby products units are dispensed when containers are correctly positioned proximate to said dispenser assembly.

9. The automated packaging apparatus of claim 1 further including an alerting system which produces visual and audio alarms indicating various conditions of the apparatus including powering up, normal operation, fault conditions, and detection of flawed or foreign products.

10. The automated packaging apparatus of claim 1, further including an analysis system comprised of a high performance computer system and associated arithmetic circuits, data acquisition circuits, a storage system configured for storing and retrieving data, a computer operating system, and a means for recording and analyzing data.

11. The automated packaging apparatus of claim 10, further including a vision inspection system comprising:
   a plurality of cameras mounted in proximity to said slats, wherein each camera is configured to capture chromatic imaging data from a specific group of said cavities;
   a plurality of servo-motors and encoders configured to precisely control the position of each camera so as to synchronize the capture of imaging data;
   means for computing and electronically recording in real time at high production speeds the visual characteristics of each product unit being dispensed by the packaging apparatus.

12. The automated packaging apparatus of claim 11, further comprising:

means for computing and electronically recording at high production speeds the weight, volume, dimensions, color, and physical integrity of each product unit within the packaging apparatus;

means for computing and electronically recording at high production speeds visual product unit flaws including incorrect colors and incorrect dimensions;

means for computing and electronically recording at high production speeds visual product unit flaws including foreign, dirty, deformed, or physically damaged product units;

means for computing and electronically recording the quantity of each said product unit being conveyed in the packaging apparatus;

means for electronically correlating and recording at high production speeds each product unit and its visual data;

means for computing and electronically recording at high production speeds the quantity of product units dispensed to each said container;

means for producing appropriate alerts and interrupting the packaging apparatus when the incorrect quantity of product units has been dispensed to any said container;

means for producing appropriate alerts and interrupting the packaging apparatus when visually flawed or foreign product units are detected;

means for creating a secure electronic audit trail of the visual product unit data.

13. The automated packaging apparatus of claim 11 wherein said cameras are installed within the packaging apparatus.

14. The automated packaging apparatus of claim 11 wherein said cameras are installed external to the packaging apparatus.

15. The automated packaging apparatus of claim 10, further including a spectroscopy inspection system comprising:
means for performing a high speed, real time analysis of the exact chemical composition of each product unit within the packaging apparatus.

16. The automated packaging apparatus of claim 15, wherein the spectroscopy inspection system comprises a high speed, production type spectroscopy system containing approximately eighty near-infrared fiber optic probes.

17. The automated packaging apparatus of claim 10, further including:
a plurality of fiber optic probes configured to capture reflected infrared spectroscopic data from said product units;
means to transmit collimated infrared beams through said fiber optic probes onto said product units;
a spectrophotometer configured to receive data from said fiber optic probes;
means to transmit spectrophotometer data to said analysis system;
means for computing and electronically recording in real time at high production speeds each product unit's dissolution measurement, hardness, and disintegration;
means for computing and electronically recording in real time at high production speeds the exact amount of active ingredients by weight of each product unit;
means for creating a secure electronic audit trail of the spectroscopic product unit data;
means for producing appropriate alerts and interrupting the packaging apparatus when chemically flawed product units are detected.

18. The automated packaging apparatus of claim 1 further including:
a bar code reader configured to scan bar code data on said containers;
means for correlating and recording visual and chemical product unit data with the product containers;
whereby product unit safety will thereby be assured.

19. An automated packaging apparatus comprising:
a reservoir configured to receive discrete product units;
a drive system;
a plurality of rotating linear elongated slats attached to said drive system, each slat having a proximal end and a distal end;
a plurality of cavities arranged along the longitudinal axis of each said slat, wherein each cavity is bifurcated by a channel passing through the cavity;
rake blade means for raking said channels in the bifurcated cavities and expelling all objects;
a control system;
a timing system;
a plurality of adjacent contoured divider plates, each divider plate configured to convey a predetermined quantity of discrete products;
a plurality of diverters proximate to the divider plates;
a diverter control assembly;
a plurality of manifolds, wherein each manifold is comprised of a plurality of adjacent funnel shaped cups arranged in a linear tier;
a plurality of linear chute tiers, wherein each chute tier is comprised of a plurality of adjacent chutes, wherein each chute is connected to the outlet of a said funnel shaped cup;
whereby discrete product units are conveyed into containers moving proximate to the outlets of the chute tiers.

20. An automated packaging apparatus comprising:
a reservoir configured to receive discrete product units;
a drive system;
a plurality of rotating linear elongated slats attached to said drive system, each slat having a proximal end and a distal end;
a plurality of cavities arranged along the longitudinal axis of each said slat, wherein each cavity is bifurcated by a channel passing through the cavity;
rake blade means for raking said channels in the bifurcated cavities and expelling all objects;
a control system;
a timing system;
dispenser means for conveying discrete products into containers moving proximate to the outlets of the dispenser means;
divider means for conveying groups of discrete products to said dispenser means.

* * * * *